United States Patent
Wright et al.

(10) Patent No.: US 6,593,123 B1
(45) Date of Patent: Jul. 15, 2003

(54) LARGE-SCALE RECOMBINANT ADENO-ASSOCIATED VIRUS (RAAV) PRODUCTION AND PURIFICATION

(75) Inventors: John Fraser Wright, Mill Valley, CA (US); Quang Qu, Alameda, CA (US)

(73) Assignee: Avigen, Inc., Alameda, CA (US)

( * ) Notice: Subject to any disclaimer, the term of this patent is extended or adjusted under 35 U.S.C. 154(b) by 0 days.

(21) Appl. No.: 09/633,834

(22) Filed: Aug. 7, 2000

(51) Int. Cl.[7] .................. C12N 7/02; C12N 15/864; C02F 1/42; B01D 15/00; B01D 15/04

(52) U.S. Cl. .............. 435/239; 435/69.1; 435/230.1; 435/803; 435/235.1; 435/240.2; 435/172.3; 210/656; 210/659; 210/660; 430/369; 430/412; 536/23.1; 536/23.5

(58) Field of Search .................. 435/239, 69.1, 435/320.1, 803, 235.1, 240.2, 172.3, 369; 530/412; 536/23.1, 23.5; 210/656, 659, 660

(56) References Cited

U.S. PATENT DOCUMENTS 6,040,183 A * 3/2000 Farrari et al. ............. 435/457

FOREIGN PATENT DOCUMENTS

| WO | WO 96/27677 | | 9/1996 |
| WO | WO 97/08298 A1 | * | 3/1997 |
| WO | WO 99/11764 | * | 3/1999 |
| WO | WO 99/61643 | | 12/1999 |
| WO | WO 00/22152 | | 4/2000 |
| WO | WO 00/23116 | * | 4/2000 |

OTHER PUBLICATIONS

Ferrari et al. Nature Medicine 1997, vol. 11, pp. 1295–1297.*
Xiao et al. J. Virology, 1998 vol. 72, pp. 2224–2232.*
Qu et al. 219th ACS National Meeting, San Francisco, CA, (Mar. 26–30, 2000), Abstract.*
Anderson et al., "A method for the preparation of highly purified adeno–associated virus using affinity column chromatography, protease and solvent extraction" *Journal of Virological Methods* 85 (2000) 23–34.
Dirk Grimm et al., *Novel Tools for Production and Purification of Recombinant Adenoassociated Virus Vectors*, Human Gene Therapy, vol. 9, Dec. 10, 1998, pp. 2745–2760.
K. Reed Clark et al., *Highly Purified Recombinant Adeno–Associated Virus Vectors Are Biologically Active and Free of Detectable Helper and Wild–Type Viruses*, Human Gene Therapy, vol. 10, Apr. 10, 1999, pp. 1031–1039.
Candace Summerford et al., *Membrane–Associated Heparan Sulfate Proteoglycan Is a Receptor for Adeno–Associated Virus Type 2 Virions*, Journal of Virology, Feb. 1998, pp. 1438–1445.
Kenji Tamayose et al., *A New Strategy for Large–Scale Preparation of High–Titer Recombinant Adeno–Associated Virus Vectors by Using Packaging Cell Lines and Sulfonated Cellulose Column Chromatography*, Human Gene Therapy, vol. 7, Mar. 1, 1996, pp. 507–513.

* cited by examiner

*Primary Examiner*—James Housel
*Assistant Examiner*—Bao Qun Li
(74) *Attorney, Agent, or Firm*—Stoel Rives LLP

(57) ABSTRACT

Methods are provided for large-scale purification of recombinant AAV (rAAV) virions that were produced in the absence of infectious adenovirus. Preferably, the rAAV is produced in a host cell line via triple-transfection with an accessory function vector, an AAV vector, and an AAV helper vector. The methods include preparing a lysate from the host cell line and passing that lysate over various combinations of ion exchange chromatography media and/or affinity chromatography media. The affinity chromatography medium is an AAV receptor or an antibody with binding affinity for AAV, e.g., heparin sulfate. A variety of cation exchange and anion exchange media are contemplated by the present invention. In certain embodiments, optional purification steps may be included, such as filtering the lysate through one or more filters, or treating the lysate with a nuclease.

21 Claims, 14 Drawing Sheets

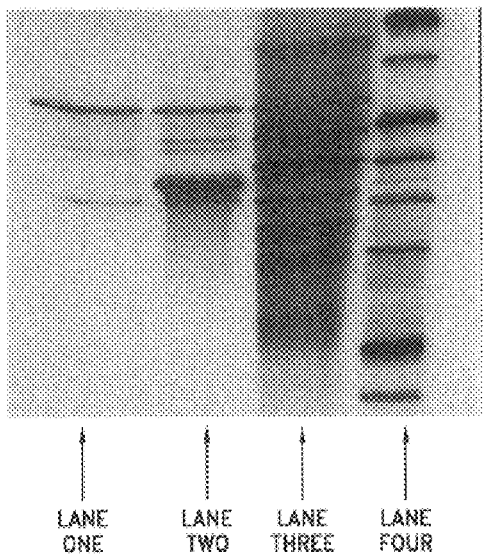 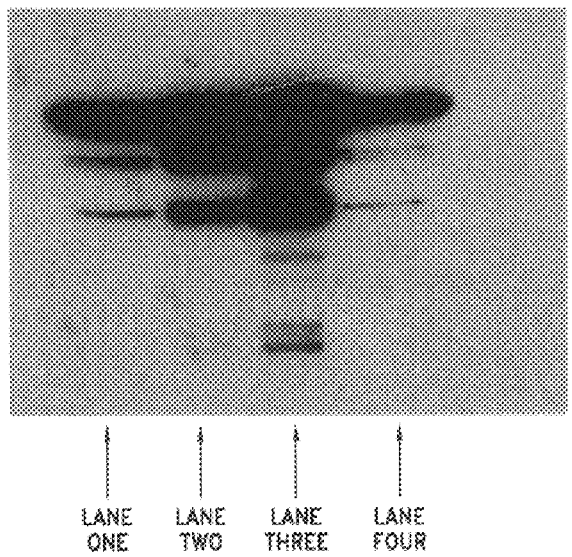
Fig. 2A
Fig. 2B
LANE ONE   LANE TWO   LANE THREE   LANE FOUR
LANE ONE   LANE TWO   LANE THREE   LANE FOUR

| Culture Apparatus | Surface Area | AAV Vector Production |
|---|---|---|
| T-flasks | 225 cm$^2$ | 2.3x10$^9$ vg/cm$^2$ |
| Standard Roller Bottles | 850 cm$^2$ | 6.5x10$^9$ vg/cm$^2$ |

Fig. 3

LARGE-SCALE RECOMBINANT ADENO-ASSOCIATED VIRUS (RAAV) PRODUCTION AND PURIFICATION

FIELD OF THE INVENTION

The invention relates to methods for producing and purifying recombinant adeno-associated virus (rAAV). More particularly, it relates to methods for producing commercial grade rAAV at large scale where rAAV was generated in the absence of infectious helper virus. The methods employ a plurality of column purification steps that yield purified rAAV. One embodiment of the invention is a two-column purification system comprising purification over an anion exchange column and over an affinity column. In another embodiment, a cation exchange column purification step is included.

BACKGROUND OF THE INVENTION

Gene delivery is a promising method for the treatment of acquired and inherited diseases. A number of viral-based systems for gene transfer purposes have been described, including adeno-associated virus (AAV)-based systems. AAV is a helper-dependent DNA parvovirus that belongs to the genus Dependovirus. AAV requires co-infection with an unrelated helper virus, e.g., adenovirus, herpes virus, or vaccinia, in order for a productive infection to occur. In the absence of a helper virus, AAV establishes a latent state by inserting its genome into a host cell chromosome. Subsequent infection by a helper virus rescues the integrated viral genome, which can then replicate to produce infectious viral progeny.

AAV has a wide host range and is able to replicate in cells from any species in the presence of a suitable helper virus. For example, human AAV will replicate in canine cells co-infected with a canine adenovirus. AAV has not been associated with any human or animal disease and does not appear to alter the biological properties of the host cell upon integration. For a review of AAV, see, e.g., Berns and Bohenzky (1987) Advances in Virus Research (Academic Press, Inc.) 32:243–307.

The AAV genome is composed of a linear, sing-stranded DNA molecule that contains 4681 bases (Berns and Bohenzky, supra). The genome includes inverted terminal repeats (ITRs) at each end that function in cis as origins of DNA replication and as packaging signals for the virus. The ITRs are approximately 145 bp in length. The internal nonrepeated portion of the genome includes two large open reading frames, known as the AAV rep and cap regions, respectively. These regions code for the viral proteins that provide AAV helper functions, i.e., the proteins involved in replication and packaging of the virion. Specifically, a family of at least four viral proteins is synthesized from the AAV rep region, Rep 78, Rep 68, Rep 52 and Rep 40, named according to their apparent molecular weight. The AAV cap region encodes at least three proteins, VP1, VP2 and VP3. For a detailed description of the AAV genome, see, e.g., Muzyczka, N. (1992) Current Topics in Microbiol. and Immunol. 158:97–129.

The construction of infectious recombinant AAV (rAAV) virions has been described. See, e.g., U.S. Pat. Nos. 5,173, 414 and 5,139,941; International Publication Numbers WO 92/01070 (published Jan. 23, 1992) and WO 93/03769 (published Mar. 4, 1993); Lebkowski et al. (1988) Molec. Cell. Biol. 8:3988–3996; Vincent et al. (1990) Vaccines 90 (Cold Spring Harbor Laboratory Press); Carter, B. J. (1992) Current Opinion in Biotechnology 3:533–539; Muzyczka, N. (1992) Current Topics in Microbiol. and Immunol. 158:97–129; and Kotin, R. M. (1994) Human Gene Therapy 5:793–801.

Contemporary rAAV virion production involves introduction of an AAV vector plasmid and an AAV helper vector plasmid into a host cell. After the AAV helper plasmid and the AAV vector plasmid bearing the heterologous nucleotide sequence of interest are introduced into the host cell (generally by stable or transient transfection), the cells can be infected with a suitable helper virus in order to provide the required accessory functions. Most typically, the helper virus will be infectious adenovirus (type 2 or type 5) or herpes virus, and will, among other functions, transactivate the AAV promoters present on the helper plasmid directing the transcription and translation of AAV rep and cap regions.

AAV vectors can be engineered to carry a heterologous nucleotide sequence of interest (e.g., a selected gene, antisense nucleic acid molecule, ribozyme, or the like) by deleting, in whole or in part, the internal portion of the AAV genome and inserting the DNA sequence of interest between the ITRs. The ITRs remain functional in such vectors allowing replication and packaging of the rAAV containing the heterologous nucleotide sequence of interest. The heterologous nucleotide sequence is also typically linked to a promoter sequence capable of driving gene expression in the patient's target cells under the certain conditions. Termination signals, such as polyadenylation sites, can also be included in the vector.

AAV helper functions can be provided in trans via an AAV helper vector. For example, such helper vectors can be plasmids that include the AAV rep and/or cap coding regions but which lack the AAV ITRs. Accordingly, such a helper vector could neither replicate nor package itself. A number of vectors that contain the rep coding region are known, including those vectors described in U.S. Pat. No. 5,139, 941, having ATCC accession numbers 53222, 53223, 53224, 53225 and 53226. Similarly, methods of obtaining vectors containing the HHV-6 homologue of AAV rep are described in Thomson et al. (1994) Virology 204:304–311. A number of vectors containing the cap coding region have also been described, including those vectors described in U.S. Pat. No. 5,139,941.

After culturing the host cells with the necessary components for rAAV production, the host cell is harvested and a crude extract is produced. The resulting preparation will contain, among other components, approximately equal numbers of rAAV virion particles and infectious helper virions. Although rAAV virion particles produced via adenovirus infection can be purified away from some of the contaminating helper virus, unassembled viral proteins (from the helper virus and AAV capsid), and host cell proteins using known techniques, such preparations contain high levels of contaminants. Approximately 95% of the contaminants are derived from adenovirus, and 50% or greater of the total protein obtained in such rAAV virion preparations is free adenovirus fiber protein. Because free adenovirus fiber protein tends to co-purify with rAAV virions, this association makes separation of the two especially difficult, lowering rAAV virion purification efficiency. Moreover, adenovirus contaminants may be particularly problematic since many adenoviral proteins, including the fiber protein, have been shown to be cytotoxic and highly immunogenic. Preparations of rAAV containing adenoviral contaminations therefore may damage the target cell or provoke undesired immune responses in the host. Varying amounts of several other unidentified adenoviral and host cell proteins are also present in the preparations. Importantly, significant levels of infectious adenovirus virions are also obtained. To inactivate the infectious adenovirus, the preparation is heat inactivated (56° C. for 1 hour). Heat inactivation, however, results in an approximately 50% drop in the titer of functional rAAV virions.

Therefore, production of rAAV virions using infectious helper viruses (such as adenovirus type-2, or a herpes virus) is undesirable for several reasons. Such production methods require the use and manipulation of large amounts of high titer infectious helper virus that present a number of health and safety concerns. Also, concomitant production of helper virus particles in rAAV producing cells diverts large amounts of cellular resources away from rAAV virion production likely lowering rAAV virion yields. Finally, the rAAV yields are even furthered lowered by the extensive purification required to remove contaminating infectious helper virus.

Current Purification Methods for rAAV

Several methods for purifying rAAV have been described in the literature. While rAAV purified by CsCl density gradients has been successfully used in human clinical trials, the method is not suitable for producing commercial scale quantities of rAAV. A method of purifying rAAV using only cationic column-chromatography has been described. However, the method fails to remove enough contaminating DNA and protein to be suitable for commercial use. A second chromatographic technique designed to purify rAAV produced using infectious adenovirus has also been described.

In order to effectively remove and/or inactivate potentially dangerous helper virus, this method involves several steps, including chromatography over anion or cation exchange columns as well as purification through tangential flow filtration or affinity purification. Even after extensive column purification, the resulting product typically will require heat inactivation to destroy any remaining helper virus particles at the expense of a substantial loss of rAAV, as much as 50%.

Because this purification system is designed primarily to remove infectious helper virus (particularly adenovirus), the system is not optimized to purify rAAV produced without infectious helper virus. Specifically, many steps are required and each of the steps results in loss of product rAAV virions, thus reducing the final yield of the recombinant product. Therefore, significant rAAV loss is unavoidable using such rAAV purification protocols increasing both the difficulty and cost of the procedure.

In sum, all prior purification systems have been designed primarily to remove and/or inactivate contaminating infectious helper virus, or are otherwise not suitable for commercial use. Thus, such systems are unsatisfactory for purifying rAAV produced in the absence of infectious helper virus, especially for large-scale production of commercial-grade rAAV. Consequently, there remains a need to provide a scalable and efficient purification system capable of separating contaminating protein and nucleic acid from rAAV prepared in the absence of infectious helper virus.

SUMMARY OF THE INVENTION

The present invention involves large-scale purification of recombinant AAV (rAAV) virions that were produced in the absence of infectious adenovirus. The methods include preparing a lysate from the host cell line then passing the lysate over various combinations of ion exchange chromatography media and/or affinity chromatography media. The host cell line is preferably cultured in roller bottles, a bioreactor, or using another technique suitable for large-scale cell culture.

In certain preferred embodiments, the rAAV is generated in a host cell line by triple-transfection with an accessory function vector, an AAV vector, and an AAV helper vector. The accessory function vector generally includes accessory functions provided by one or more adenovirus early region sequences, particularly, the E1b, E2a, E4, and/or VA RNA regions. The AAV vector includes one or more heterologous nucleotide sequences of interest flanked by at least one functional inverted terminal repeat (ITR) sequence. Finally, the AAV helper vector generally includes the AAV rep and/or the AAV cap sequences. In certain embodiments, the AAV helper vector may also have a modified AAV p5 promoter. After harvesting the transfected cell line, a lysate is formed using techniques suitable for large-scale production, such as microfluidization.

The affinity chromatography medium used for purifying rAAV will preferably be an AAV receptor or an antibody with binding affinity for AAV. In a preferred embodiment, heparin sulfate is used as the affinity chromatography medium. A variety of cation exchange and anion exchange media are contemplated for use with the present invention. Suitable cation exchange media include sulfo-, phospho, carboxy-, and carboxy-methyl-based resins. In one embodiment, a cation exchange chromatography module is used that contains a medium known as MUSTANG S™. Suitable anion exchange media include N-charged amino or imino resins such as STREAMLINE Q XL™, MUSTANG Q™, POROS 50 PI, SEPHAROSE Q, any DEAE, TMAE, tertiary or quaternary amine, or PEI-based resins.

Several optional purification steps may also be used with the present methods, such as filtering the lysate through one or more filters or treating the lysate with a nuclease. In the certain embodiments, the methods are optimized to purify rAAV that was produced in a host cell line cultured in the absence of serum.

BRIEF DESCRIPTION OF THE DRAWINGS

FIG. 2 is a Western blot showing concentration of capsid proteins following purification.

FIG. 3 is a comparison of AAV production in T-flasks versus roller bottles.

DETAILED DESCRIPTION OF THE PREFERRED EMBODIMENT

Figure 1:
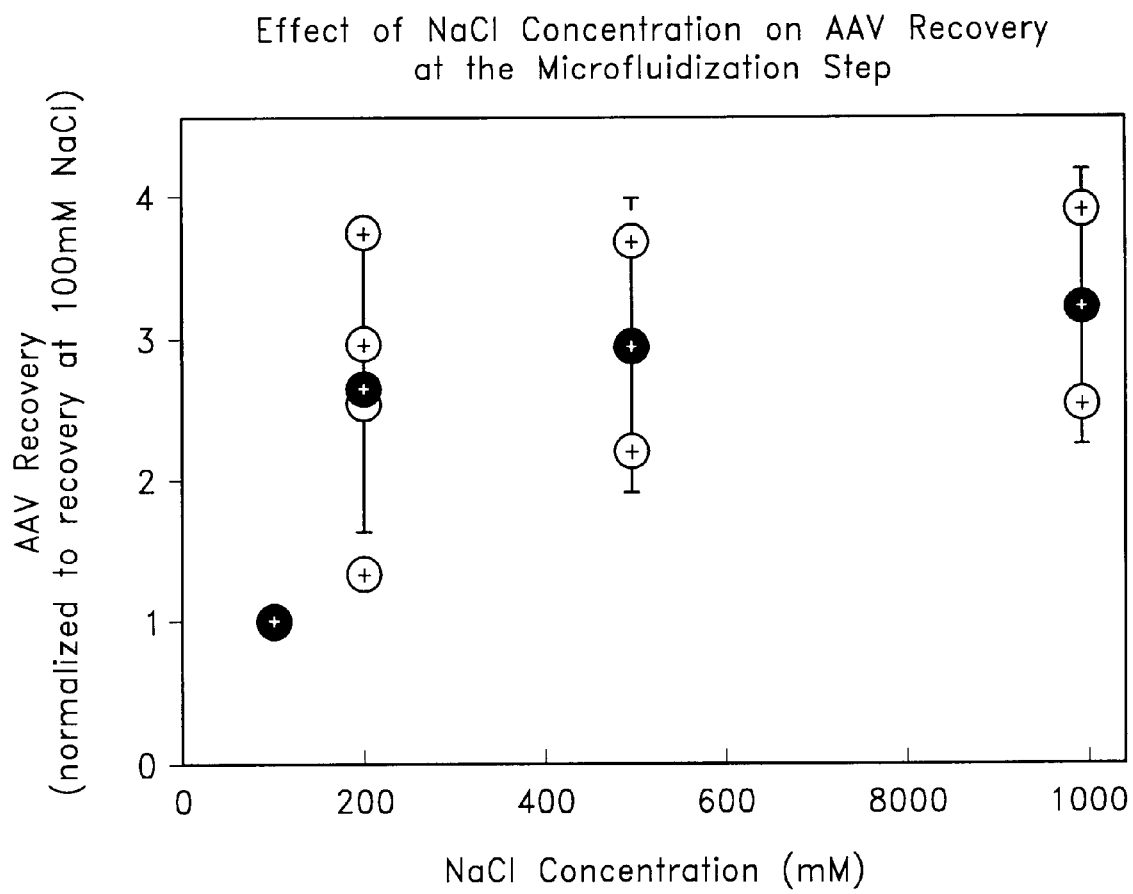
FIG. 1 shows the effect of NaCl concentration on AAV recovery at the microfluidization step.

The invention disclosed herein involves methods for producing and purifying recombinant adeno-associated virus (rAAV) virions or particles at large-scale. Large-scale production methods are necessary to permit the use of rAAV as a gene therapy vector in large clinical trials and/or in a commercial setting. The methods of the disclosed invention are also designed to purify rAAV that was produced without infectious helper virus.

Unless otherwise indicated, the disclosed invention will employ conventional methods of virology, microbiology, molecular biology and recombinant DNA techniques that are well known to those of ordinary skill of the art. Such techniques are explained fully in the literature. See, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijessen, ed.); Fundamental Virology, 2nd Edition, vol. I & II (B. N. Fields and D. M. Knipe, eds.).

In one embodiment of the present invention, the rAAV virions or particles to be purified are produced by culture of suitable host cells following the triple-transfection of such cells with AAV vector, AAV helper vector, and accessory function vector. By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors. The AAV nucleotide sequence used in constructing the AAV vectors and the AAV helper vectors can be derived from any adeno-associated virus serotype, including without limitation, AAV-1, AAV-2, AAV-3, AAV-4, AAV-5, and AAVX7.

AAV Vectors

AAV vectors generally have one or more of the AAV wild-type genes deleted in whole or part, preferably the rep and/or cap genes, but retain at least one functional flanking inverted terminal repeat (ITR) sequence. Thus, such AAV vectors can be constructed to include one or more heterologous nucleotide sequences flanked directly or indirectly by one or more ITRs.

Functional ITR sequences are required in cis for the rescue, replication and packaging of the rAAV virion. While the nucleotide sequences of AAV ITR regions are known, (See, e.g., Kotin, R. M. (1994) Human Gene Therapy 5:793–801; Berns, K. I. "Parvoviridae and their Replication" in Fundamental Virology, 2nd Edition, (B. N. Fields and D. M. Knipe, eds.) for the AAV-2 sequence), the ITRs employed in the present invention need not correspond to an AAV wild-type nucleotide sequence. That is, the ITRs may be altered by the insertion, deletion or substitution of nucleotides, so long as the sequences function in the rescue, replication and packaging of rAAV. Also, the AAV ITRs may be derived from any of several AAV serotypes, including without limitation, AAV-1, AAV-2, AAV-3, AAV-4, AAV-5, AAV-6, and AAVX7. Finally, when more than one ITR is used in an AAV vector, those ITRs need not be identical or derived from the same AAV serotype or isolate, so long as they function as intended.

The recombinant genome of the AAV vector can be constructed using standard molecular biology techniques that are well known in the art. For example, see, U.S. Pat. No. 5,173,414; International Publication Nos. WO 92/01070 (published Jan. 23, 1992) and WO 93/03769 (published Mar. 4, 1993); Lebkowski et al. (1988) Molec. Cell. Biol. 8:3988–3996; Vincent et al. (1990) Vaccines 90 (Cold Spring Harbor Laboratory Press); Carter, B. J. (1992) Current Opinion in Biotechnology 3:533–539; Muzyczka, N. (1992) Current Topics in Microbiol. and Immunol. 158:97–129; Kotin, R. M. (1994) Human Gene Therapy 5:793–801; Shelling and Smith (1994) Gene Therapy 1:165–169; and Zhou et al. (1994) J. Exp. Med. 179:1867–1875.

AAV vectors can also include control sequences, as well as selectable markers or reporter genes, enhancer sequences, and other control elements that allow for the induction of transcription. The term "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need be present so long as the selected gene is capable of being replicated, transcribed and translated in an appropriate recipient cell.

Heterologous Nucleotide Sequences

In the context of the present invention, "heterologous nucleotide sequences" generally refers to nucleic acid sequences such as coding sequences and control sequences that are not normally joined together, and/or are not normally associated with a particular cell.

The selected heterologous nucleotide sequence used in the AAV vector can comprise any desired gene that encodes a protein that is defective or missing from a recipient cell genome. Alternatively, the selected heterologous nucleotide sequence can encode a native or non-native protein having a desired biological or therapeutic effect (e.g., an antiviral function). Suitable genes for use in the AAV vector include those used for the treatment of inflammatory diseases, autoimmune, chronic and infectious diseases, including such disorders as AIDS, cancer, neurological diseases, cardiovascular ease, hypercholestemia; various blood disorders including various anemias, thalasemias and hemophilia; genetic defects such as cystic fibrosis, Gaucher's Disease, adenosine deaminase (ADA) deficiency, emphysema, etc. Heterologous nucleic acid sequences considered particularly well-suited for use in an AAV vector include sequences that encode the following proteins: Hemophilia B Factor IX, Hemophilia A Factor VIII, Gaucher's Disease Glucocerbrosidase, Sly's Syndrome Beta-Glucuronidase, Hurler's Alpha-Iduronidase, Hereditary Emphysema alpha-1 Antitrypsin, Beta-Thalassemia EPO, and Parkinson's Diseases Tyrosine kinase & AADC. Heterologous coding sequence may also comprise synthetic sequences having codons different from the native gene.

In certain embodiments, the selected nucleotide sequence can correspond to a molecule having an antisense or ribozyme function. A number of antisense oligonucleotides (e.g., short oligonucleotides complementary to sequences around the translational initiation site (AUG codon) of an mRNA) that are useful in antisense therapy for cancer and for viral diseases have been described in the art. See, e.g., Han et al. (1991) Proc. Natl. Acad. Sci. USA 88:4313–4317; Uhlmann et al. (1990) Chem. Rev. 90:543–584; Helene et al. (1990) Biochim. Biophys. Acta. 1049:99–125; Agarwal et al. (1988) Proc. Natl. Acad. Sci. USA 85:7079–7083; and Heikkila et al. (1987) Nature 328:445–449. For a discussion of suitable ribozymes, see, e.g., Cech et al. (1992) J. Biol. Chem. 267:17479–17482 and U.S. Pat. No. 5,225,347 to Goldberg et al.

AAV Helper Vectors

AAV helper vectors can be used to provide transient expression of AAV rep and/or cap genes, thereby complementing the missing helper functions of the rAAV vector. AAV helper vectors can be in the form of a plasmid, phage, transposon, cosmid, virus, or virion. A number of AAV helper vectors have been described, such as the commonly used plasmids pAAV/Ad and pIM29+45 which encode both Rep and Cap expression products. See, e.g., Samulski et al. (1989) J. Virol. 63:3822–3828; and McCarty et al. (1991) J. Virol. 65:2936–2945. A number of other vectors have also been described which encode Rep and/or Cap expression products. See, e.g., U.S. Pat. No. 5,139,941.

Due to homologous recombination events between the AAV ITR sequences present in the AAV vector and the AAV helper function sequences present in the helper construct, the use of certain constructs could potentially generate contaminating wild-type AAV virions in the rAAV virion stocks. The presence of such wild-type AAV particles in AAV-based vector systems could lead to the unintentional spread of recombinant AAV virions or could interfere with the efficient expression of foreign genes. (The most likely problem is that wt-AAV will outgrow rAAV in the production thereby lowering the yield of rAAV.)

To avoid generating wild-type AAV particles, the disclosed invention contemplates the use of nucleic acids encoding AAV helper functions as described in U.S. Pat. No. 6,001,650, hereby incorporated by reference. Specifically, in certain embodiments of the disclosed invention, an AAV helper construct is used that includes an AAV rep coding region, an AAV cap coding region, and a modified AAV p5 promoter that lacks an intact TATA box. In particular embodiments, the modified p5 promoter is located 3' relative to the rep coding region. The use of such constructs will minimize or eliminate homologous recombination events and thus minimize the formation of wild-type AAV particles.

Accessory Function Vectors

AAV production generally requires coinfection with an unrelated helper virus (e.g., an adenovirus, a herpes virus or a vaccinia virus) in order to supply necessary "accessory functions." For example, it has been demonstrated that adenovirus supplies factors required for AAV promoter expression, AAV messenger RNA stability and AAV translation. See, e.g., Muzyczka, N. (1992) Curr. Topics. Microbiol. and Immun. 158:97–129. In the absence of these "accessory functions," AAV establishes a latent state by insertion of its genome into a host cell chromosome. On the other hand, upon supply of these accessory functions, the integrated copy is rescued and can replicate to produce infectious viral progeny.

Rather than using infectious helper virus to provide the necessary accessory functions, the present invention contemplates that the accessory functions will be provided on a replication-incompetent accessory function vector. In certain preferred embodiments, the accessory function vector(s) will include adenoviral-derived nucleotide sequences necessary for rAAV virion production. Such sequences can include E1a, E1b, E2a, E4 and VA RNA regions.

More specifically, U.S. Pat. No. 6,004,797, incorporated by reference herein, describes the production of rAAV without infectious helper virus. For example, instead of infecting with infectious adenovirus, the host cell is transfected with one or more vectors having nucleotide sequences from an adenovirus type-2 or type-5 genome that are required for rAAV replication and packaging but are insufficient to make infectious adenovirus. These nucleotide sequences include (i) adenovirus VA RNAs, (ii) an adenovirus E4 ORF6 coding region, (iii) an adenovirus E2a 72 kD (coding for the E2a 72 kD DNA-binding protein), or any combination of nucleotide sequences (i), (ii), and (iii). Alternatively, one or more accessory function vectors can provide other nucleotide sequences encoding accessory functions. Importantly, these accessory function vectors lack most of the adenovirus genome, including the fiber protein. Production of rAAV in this manner, i.e., without infectious helper virus, minimizes the health and safety concerns.

While not being bound by any particular theory, the accessory functions provided by the adenovirus E1b, E2a, and E4 early genes are thought to be required in AAV DNA replication. The accessory functions provided by the adenovirus E1b, E4, and VA RNA gene regions appear to participate in post-transcriptional or translational events in the AAV life cycle. Regarding the accessory functions provided by E4, only the E4 34 kD protein encoded by open reading frame 6 (ORF 6) of the E4 coding region is clearly required for AAV replication. The accessory functions provided by the adenovirus gene region E1a are thought to be required as modulators to activate transcription or expression of the other adenovirus gene regions, including E1b, E2a, E4 and VA RNA.

The accessory function vectors of the invention can alternatively include one or more polynucleotide homologue (s) that replace the adenoviral gene sequences, so long as each homologue retains the ability to provide the accessory functions of the replaced adenoviral gene. Thus, homologous nucleotide sequences can be derived from another adenoviral serotype (e.g., adenovirus type-2), from another helper virus moiety (e.g., a herpesvirus or vaccinia virus), or can be derived from any other suitable source.

Further, accessory function vectors constructed according to the invention can be in the form of a plasmid, phage, transposon or cosmid. Alternatively, the vector can be in the form of one or more linearized DNA or RNA fragments that, when associated with the appropriate control elements and enzymes, can be transcribed or expresses in a host cell to provide accessory functions.

Accessory functions vectors can be engineered using conventional recombinant techniques. Particularly, nucleic acid molecules can be readily assembled in any desired order by inserting one or more accessory function nucleotide sequences into a construct, such as by ligating restriction fragments into a cloning vector using polylinker oligonucleotides and the like. The newly formed nucleic acid molecule can then be excised from the vector and placed in an appropriate expression construct using restriction enzymes or other techniques that are well known in the art.

Members of herpesviridae are also known to act as AAV helper viruses. In alternative embodiments of the disclosed invention, particular sequences from herpesviridae capable of assisting in the production of AAV in a host cell can be used in an accessory function vector.

In alternative embodiments, rAAV may be produced using various cell lines that possess AAV helper and/or accessory functions necessary to produce rAAV particles, thus obviating the need for transduction with helper and/or accessory function vectors.

Large-Scale Cell Culture for rAAV Production

One major obstacle in producing rAAV virions for large clinical trials and commercial use involves the present lack of commercially feasible large-scale cell culture techniques. The disclosed invention contemplates the use of various tissue culture devices that are amenable for use with large-scale cell-culture protocols. Examples of suitable tissue culture devices include the use of bioreactors and roller-bottles. One type of bioreactor is a cell culturing apparatus that has a cylindrical tank and a stirring apparatus to circulate cells and culture medium. Bioreactors are capable of producing high-density cell cultures, which in turn produce large amounts of rAAV after purification. Roller-bottles are cylindrical tissue culture bottles that are rotated at a given periodicity. The advantage of using roller-bottles in cell culture is that roller-bottle techniques are scaleable and thus decrease the labor and the costs of virion production. Moreover, roller-bottles are disposable, obviating laborious cleaning and sterilization and simplifying post-production facility validation. The roller bottles used are available commercially and a variety of bottles having different culture surface areas are available. The methods of the disclosed invention are not limited by the surface area of any particular roller bottle. Accordingly, various sizes of roller bottles are contemplated for use with the disclosed invention.

A variety of cells lines are contemplated for use in the large-scale production of rAAV. Particularly suitable for cell culture of rAAV is Human Embryo Kidney (HEK) 293 adherent cell lines. Examples of other suitable cell lines to produce rAAV include: Vero cells, HeLa cells, and CHO cell lines. As used herein, the term "cell line" refers to a population of cells capable of continuous or prolonged growth and division in vitro. Often, cell lines are clonal populations derived from a single progenitor cell. It is known in the art that spontaneous or induced changes can occur in karyotype during storage or transfer of such clonal populations. Therefore, cells derived from the cell line referred to may not be precisely identical to the ancestral cells or cultures. Nevertheless, the term "cell line" includes such variants.

Once a cell line is selected, the tissue culture device of choice is seeded with cells at a density suitable to support cell culture. The density of cells used to seed a particular device will depend on the size of the device. For example, when the cell culture device is a roller-bottle with a surface area of about 850 cm$^2$, a cell density of between $1\times10^4$–$1\times10^9$ cells/bottle is used to seed the bottle. In certain preferred embodiments, roller-bottle having a surface area of about 850 cm$^2$ are seeded with cells ranging from between $1\times10^7$–$1\times10^8$, or in one particularly preferred embodiment, such bottles are seeded at a density of about $2\times10^7$ cells/bottle.

A variety of volumes may be used to grow the cells in the tissue culture device of choice. The volume of medium used will vary according to the size of the tissue culture device used to grow the tissue culture cells. When a roller-bottle with a surface area of about 850 cm$^2$ is used as the tissue culture device, the cells are preferably grown in a volume of approximately 200 ml.

Various growth media may be used in the disclosed invention to achieve large-scale cell growth. In one embodiment, Delbeco's Modified Eagle's Medium (DMEM) culture fluid supplemented with 4.5 grams per liter of glucose and 10% fetal calf serum is used to grow the tissue culture cells of choice. The selection of growth medium varies depending on the type of cells being cultured. One of skill in the art will appreciate that there are many alternatives to DMEM, that other volumes of culture media may be used (preferably between 100–500 mls), and that the media may be supplemented with anywhere from 0–20% fetal calf serum. (See WO 00/22152, which is hereby incorporated by reference).

Introduction of Vectors into Tissue Culture Cells

The vectors of the disclosed invention can be introduced into a cell using a variety of transfection techniques. Such transfection methods have been described in the art, including calcium phosphate co-precipitation (Graham et al. (1973) Virol. 52:456–467), direct micro-injection into cultured cells (Capecchi, M. R. (1980) Cell 22:479–488), electroporation (Shigekawa et al. (1988) BioTechniques 6:742–751), liposome mediated gene transfer (Mannino et al. (1988) BioTechniques 6:682–690), lipid-mediated transfection (Felgner et al. (1987) Proc. Natl. Acad. Sci. USA 84:7413–7417), and nucleic acid delivery using high-velocity microprojectiles (Klein et al. (1987) Nature 327:70–73). Other acceptable transfection media include strontium phosphate, polycationic polymers, e.g., Superfect (QIAGEN™), liposomes, and polyethyleneimine (PEI). (See e.g, WO 00/22152).

Any of these techniques can be used to introduce one or more exogenous DNA moieties, such as AAV helper constructs, AAV vector plasmids, and other vector constructs into suitable host cells. Generally, the exogenous DNA must traverse the host cell plasma membrane in order to be exposed to the cell's transcription and replication machinery. The resulting cell can be transiently transfected with the exogenous nucleic acid molecule, i.e., the exogenous DNA will not be integrated into the genome of a transfected cell, but rather will exist episomally. Alternatively, the resulting cell can be stably transfected, i.e., the nucleic acid molecule will become covalently linked with the host cell genome or will be maintained and replicated as an episomal unit which can be passed on to progeny cells (e.g., capable of extra-chromosomal replication at a sufficient rate).

In one embodiment of the invention, the host cells of choice are triple-transfected with at least one vector encoding a heterologous nucleotide sequence, of interest, at least one vector encoding AAV helper functions, and at least one vector encoding viral accessory functions. Triple-transfection is preferably done using a standard calcium-phosphate mediated transfection (Graham et al., 1973, J. Virol. 33:739–748) or PEI transfection.

Triple-transfection is preferably done at day-two post cell seeding. However, transfection can alternatively occur on the day cell seeding is performed, or may be done on day one, day two, day three, day four, or day five post cell seeding depending on the cell seeding density. The cell culture medium is then typically harvested at day three post-transfection. However, the cells and culture medium containing the transfected cells may alternatively be harvested on day zero through day five following transfection, more preferably between day two and day four following transfection.

Once harvested, the cells are analyzed for rAAV production using various techniques well known in the art. For example, quantitative PCR may be used to analyze culture medium for rAAV production. Typically, production in roller bottles will yield between $1 \times 10^9$ and $5 \times 10^{10}$ vector genomes (vg)/cm2.

Concentration of Cells and Buffer Exchange

Following harvest, the cell culture-containing medium is often in a large volume. Purification of viral particles from the cells contained in the large volume of culture medium, typically 100 liters or more, is time sensitive and labor intensive. Although not an essential step in the production and purification of rAAV, several techniques can be used to concentrate the rAAV viral particles, thus simplifying the post-harvest or downstream processing of the cell culture medium. One technique contemplated by the present invention is continuous centrifugation. Continuous centrifugation of the cell culture is performed in order to reduce the volume of the culture and to permit the buffer exchange that can, in particular embodiments, facilitate further downstream processing. Through the process of continuous centrifugation, the volume of cell culture medium will generally be reduced 10-fold, thus, for example, reducing the medium containing the cells of interest from 100 liters down to about 10 liters. In other embodiments, the cell culture medium is reduced between 2-fold and 100-fold.

The concentration/buffer exchange protocol can also be utilized to wash the transformed cells. In one embodiment, the cells are washed with an appropriate buffer to facilitate further downstream processing. The washing of the cells serves to eliminate various waste products and culture medium components that might otherwise contaminate the final preparation of rAAV particles. Several suitable buffers are well known in the art, including various phosphate and bicarbonate buffers. Following condensation and buffer exchange, the cells are ready to be lysed in order to recover the rAAV.

Cell Lysis

Several techniques are contemplated by the disclosed invention to achieve lysis of the harvested and concentrated cultured cells. Examples of suitable cell lysis protocols include: sonication, multiple freeze/thaw cycles, and osmotic shock. For the purposes of large-scale purification, however, mechanical lysis, using a Microfluidizer™ (Microfluidics International Corp., Newton, Mass.), is a more efficient way to prepare the cell lysate in large scale.

The buffer systems used for cell lysis has been found to significantly affect the efficiency of rAAV release from the cells. One condition of particular interest is the osmolality of the solution. In certain embodiments, modification of the ion concentrations can be used to alter the osmolality of the solution and facilitate cell lysis and rAAV release. For example, increasing amounts of NaCl correlate with an increase in rAAV vector release. As shown in FIG. 1, when normalized to the number of rAAV particles released at 100 nM NaCl, a 2.6-fold, 2.9-fold and 3.2-fold increase in rAAV release is observed at 200 nM, 500 nM and 1 M NaCl concentrations, respectively. One skilled in the art will appreciate that other compounds could be used to alter the osmolality of the buffer solution.

In one preferred embodiment of the invention, the cells are re-suspended in a phosphate buffer containing 20 mM sodium phosphate and 200 mM NaCl at pH 7.4, and lysed by subjecting the cells to multiple rounds of homogenization or other mechanical stress (e.g., Microfluidizer™). The total virus recovered from this technique is comparable or better than that obtained using multiple freeze and thaw cycles. Furthermore, this method permits passing the cells at a flow rate about 650 ml/minute. Consequently, the methods of the disclosed invention are suitable for accommodating a large volume of cells and, when used with the preferred buffer conditions, can be used to achieve a high efficiency of cell lysis and rAAV release.

Clarification

The lysate produced from the lysis of the rAAV-containing cultured cells will generally be clarified before further downstream purification steps are performed. Several clarification techniques are known that can be used in rAAV purification, including centrifugation and tangential flow filtration. Alternatively, the cell lysate can be clarified by filtration using one or more filters of varying pore size. Suitable clarification techniques will permit a high throughput of lysate, provide ease of use, are scaleable for use with large volumes, and result in superior viral vector recovery.

In one preferred embodiment, the cell lysate is filtered through a 2.0 $\mu$m ULTIPLEAT PROFILE™ filter and then filtered through a 0.45 $\mu$m SUPOR™ membrane filter (Pall Corporation, Port Washington, N.Y.) at a flow-rate of 120 ml per minute. Using this technique, up to 100% rAAV recovery may be achieved. Following filtration, the sample is ready for chromatography purification.

Chromatography

The disclosed invention contemplates using a plurality of chromatographic steps in order to purify rAAV particles from cellular debris. Three modes of chromatography, used in varying orders and combinations, are contemplated by the present invention: cation exchange chromatography, anion exchange chromatography, and affinity chromatography. The invention also contemplates many support medium, including agarose, cellulose, silica, and poly(stryrene-divinylbenzene) (PSDVB). In addition multiple chromatographic methods can be used including conventional chromatography, HPLC (High Performance Liquid Chromatography or High pressure Liquid Chromatography), or perfusion chromatography. One skilled in the art will also appreciate that the size of the column (i.e., diameter and length) will depend on several factors such as the volume of material to be loaded, the concentration of rAAV to be purified, and the desired resolution or purity.

In cation exchange chromatography a negative functional group is bound to the insoluble support medium. Accordingly, cation exchange chromatographic media bind positive counter ions when the incubation period is a sufficient time period to allow for the positively charged groups to bind to and come to equilibrium with the negatively charged cation exchanger medium. Neutral molecules and anions do not bind to the cation exchange medium. Following the electrostatic binding of species possessing a net positive charge, the cationic medium is washed, removing non-binding molecules from the medium. Bound ions are then eluted either by washing the medium with increasing concentrations of positive ions or by altering the pH of the medium. The disclosed invention contemplates using a variety of cation exchange media such as any sulfo-, phosphor carboxy-, or carboxy-methyl-based cation exchange resins bound to numerous support medium well known in the art.

In one embodiment, the cation exchanger is a commercially available cation exchange module contains a sulfo-based material called MUSTANG S™ (Pall Membrane Technology Corporation, Pensacola, Fla.). The material has the typical cation exchanger function, but instead of using typical beads as solid phase to link the functional group, a membrane-based solid phase is used. This material is very robust and allows a high flow-rate for purification due to the pore size of the membrane. rAAV binds to the MUSTANG S™ cation exchanger in a 20 mM sodium phosphate buffer solution at pH 6.0 having a salt concentration below 200 mM NaCl. The rAAV can be eluted at salt concentration above 250 mM NaCl in the same phosphate buffer. Under these conditions, the rAAV is purified more than 1000-fold and routinely greater than 80% of the rAAV material loaded is recovered.

Anion exchange chromatography is analogous to cation exchange chromatography except that a positive functional group is bound to the insoluble support medium. Several possible anion exchange media are known that can be used in such columns including N-charged amino or imino resins such as POROS 50 PI™, Q SEPHAROSE™, any DEAE, TMAE, tertiary or quaternary amine, or PEI-based resin. One of skill in that art will appreciate that isolated recombinant rAAV can be purified on an anion exchange column either before or after purification on other columns.

In one embodiment of the present invention, an anion exchange column is used that contains a material called STREAMLINE Q XL™ (Pharmacia, Piscataway, N.J.). This material has a strong anion exchanger function as well as a high loading capacity and a high chemical stability so that it can be used over a wide pH range. In passing rAAV-containing material through a STREAMLINE Q XL™ column at 7.0–8.5 pH and under 200 mM NaCl conditions, the rAAV flows through the column while much of the contaminating protein remains bound to the column. Under these conditions, the rAAV is purified more than 2–3 fold and routinely greater than 90% of the rAAV material loaded is recovered.

Affinity chromatography is a technique that provides for ligand specific purification of a target compound. As such, the technique exploits the structural and functional characteristics properties of macromolecules by binding the molecules based on these specific characteristics under certain conditions.

A variety of different affinity column matrices are contemplated for use with the disclosed invention. For example, antibodies directed against coat proteins of rAAV may be used to generate affinity column media that in turn can be used to purify rAAV. Another example of an affinity column utilizes one or more cell receptors of AAV. These receptors can often be produced and used to generate affinity column media.

A number of molecules are thought to serve as AAV receptors. For example, AlphaV-beta5 integrin (Summerford, C., et al., *Nat Med* January 5:1 78–82 (1999)), human fibroblast growth factor receptor 1 (Qing K, et al., (*Nat Med* January 5:1 71–7 (1999)), and a membrane-associated heparin sulfate proteoglycan (Summerford & Samulski, *J Virol.* February 72:2 1438–45 (1998)), have all been reported as AAV receptors. Any of these receptors or other receptor molecules can be used to generate affinity chromatography media.

One embodiment of the disclosed invention contemplates the use of heparin as the adsorbent group. Affinity chromatography media containing heparin are commercially available from a variety of sources. For example, PerSeptive Biosystems, Inc. (Framingham, Mass.) markets a heparin-based medium (POROS 20HE™). When POROS 20HE™ is used as the affinity chromatography medium, the rAAV containing solution is applied to the affinity medium and subsequently eluted with an appropriate salt concentration.

rAAV binds to the POROS 20HE™ at a salt concentration of about 250 mM or less NaCl in the 20 mM phosphate buffer at pH 7.4 and starts to elute at 300 mM NaCl, but elutes more efficiently at salt concentrations of 400 mM NaCl or higher in the same buffer. Following loading of rAAV-containing material, the affinity chromatography medium can be washed with an anionic detergent, such as 5–15 mM sarcosine or 0.5% sodium deocholatic acids having a salt concentration of between 150–300 mM NaCl in order to remove protein contaminants from the final rAAV product. In one specific embodiment, rAAV containing samples in 20 mM phosphate/250 mM NaCl at pH 7.4 were loaded on POROS 20HE™ affinity columns and the columns were washed with 3 times the bed volume of 100 mM NaCl, 20 mM phosphate buffer at pH 7.4 buffer containing either 6M urea, 0.5% deocholate acid, or 15 mM sarcosine. The rAAV was eluted from the columns with 3 bed volumes of 20 mM phosphate/400 mM NaCl at pH 7.4, and the various eluates were compared for protein contaminants by silver-stained SDS PAGE. Referring to FIG. 2(*a*), lane 4 is a MW marker, lane 3 is 6M urea washed sample, lane 2 is 0.5% deoxycholate acid washed sample, and lane 1 is a 15 mM sarcosine wash. The sarcosine wash removed the most contaminants from the rAAV preparation. To verify that the bands on the SDS PAGE gel in fact represented rAAV capsid proteins PV1, VP2, and VP3, a Western blot was run using primary monoclonal antibodies to VP1, VP2, and VP3 conjugated with Horseradish peroxidase (shown in FIG. 2(*b*)). Typically, greater than 50 percent of the rAAV is recovered from heparin affinity chromatography under these conditions.

Certain embodiments of the disclosed invention contemplate the use of a cation exchange medium in conjunction with an affinity chromatography medium to purify rAAV particles from the cellular milieu released during the lysis process. In one embodiment, the cell lysate is loaded on a cation exchanger module containing the MUSTANG S™ medium (Pall Membrane Technology Center, Pensacola, Fla.). Such modules are available commercially in a variety of sizes, including 10 ml and 100 ml. Following purification over the cation exchange module or column, the rAAV-containing material is passed over a heparin-based resin. The column is then washed and eluted. The purified sample of virions can be analyzed by silver-stained SDS-PAGE for purity.

An alternative embodiment of the invention uses an anion exchange medium in conjunction with an affinity medium in order to purify rAAV particles for pharmacological use. For example, a rAAV lysate can be prepared having a concentration of approximately 200 mM NaCl and that lysate can be passed over an anion exchange column, such as STREAMLINE Q XL™, MUSTANG Q™ (module), POROS 50 PI™, Q SEPHAROSE™, any DEAE, TMAE, tertiary or quaternary amine, or PEI-based resins. In addition to achieving a high level of purification, the MUSTANG Q™ module also permits high flow-rate processing.

rAAV is generally recovered from an anion exchange step in the flow-through fractions (depending on the pH). The salt concentration and pH of such flow-through fractions can then be adjusted for purification over a heparin column or for purification over any other suitable affinity column. It should be noted that the order of the chromatographic media is not considered to be important to the ultimate purification of the rAAV particles. Also, a cation exchange column may optionally be used to further purify the sample, and treatment with a nuclease can be used, but is not required. The yields obtained using such combinations are predictable based on the yields obtained using the individual column-purification steps.

rAAV eluted from an ion exchange column and/or affinity column can be subjected to additional ion exchange or affinity purification steps (i.e., polishing) as required. In one embodiment of the invention, eluate purified by combination cation exchange chromatography and affinity chromatography was polished by passage over a 16 mm diameter POROS 50 PI™ anion exchange column (Applied Bioscience, Foster City, Calif.) having a volume of 1.6 mL at a flow rate of approximately 150 cm/hr. rAAV does not bind to the column at a salt concentration of 400 mM NaCl and at a pH of between 5.5 and 7.4. DNA and other residual proteins bind to the anionic exchange membrane.

Nucleic Acid Digestion

An optional purification step contemplated in certain embodiments of the disclosed invention addresses the issue of DNA contamination of the final rAAV product. During the lysis procedure, large amounts of cellular DNA are released into the lysate. This material may affect the purity of the final rAAV composition. One option for reducing the DNA contamination from the final rAAV products is to digest the DNA before or during the chromatography purification steps.

A variety of DNA digestion methods are contemplated for use in the disclosed invention. For example, enzymatic and chemical means of DNA digestion are contemplated for use with the methods of the disclosed invention. Typically, DNA is digested with nuclease, such as DNase I™ or BENZONASE™, (E.M. Science, Gibstown, N.J.) before the purification process.

In one embodiment of the disclosed invention, BENZONASE™ is used to digest DNA during the large-scale rAAV purification process. The digestion may occur before, after, or during the first chromatographic purification step. For example, the rAAV containing cell lysate may be treated with BENZONASE™ prior to or during a step at which rAAV particles are applied to a cationic exchange medium. Specifically, when that medium is MUSTANG S™, the rAAV will bind to the membrane whereas contaminant DNA and other contaminants will fail to bind and will be subsequently washed from the membrane.

In theory, DNA should not bind the MUSTANG S™ membrane. Nevertheless, there is a possibility that residual DNA will bind to the membrane due to non-specific binding. To remove such DNA contamination, techniques have been developed to treat the sample during the purification while the rAAV is bound to the module S. That is, BENZONASE™ at a concentration of 200 U/ml can be used to wash the MUSTANG S™ membrane after the sample is loaded. Given the fact that BENZONASE™ does not bind to cationic exchangers, BENZONASE™ can be removed from the MUSTANG S™ by washing the module thoroughly.

Virus Product Concentration

The rAAV produced by the above-described methods may optionally be concentrated for storage and use. A number of concentration protocols are contemplated by the present invention, including tangential flow filtration. One skilled in the art will appreciate that many membranes are commercially available in an extensive range of molecular weight cutoffs or pore sizes.

EXAMPLES

Particular aspects of the present invention may be more readily understood by reference to the following examples, which are intended to exemplify the invention, without limiting its scope to the particular exemplified embodiments.

Example 1

Cell Culture

In a sterile environment such as a biosafety cabinet (BSC), Human Embryo Kidney (HEK) 293 cells suspended in 200 milliliters of Dulbecco's Modified Eagle's Medium (DMEM) (10% Fetal Calf Serum (FCS), 1 mM glutamine) were added to each of 10 two liter roller bottles (850 cm$^2$ cultivable surface area) at a quantity of 50,000,000 cells per bottle. Alternatively, the cells were suspended in a smaller quantity of supplemented growth medium, added to the roller bottles, and medium added to each bottle to give a final volume of 200 mL. The air in the roller bottles was displaced with a mixture of 5% $CO_2$ in air using a sterile pipette connected to a source of 5% $CO_2$/air, and the bottles were capped tightly. The roller bottles were placed in a roller bottle rack set at a rotation rate of 0.2 revolutions per minute, in a temperature-controlled environment.

The roller bottles were incubated for 3 days at 37° C. At the end of this incubation period, the roller bottles were removed to a BSC, caps removed, and a solution of calcium phosphate containing equal quantities of purified bacterial plasmid vectors encoding rAAV sequences, helper functions, and accessory functions were added. In particular, 1500 µg of each of plasmids pHLP19, pLadeno5, and hFIX9, were added to 150 mL of a 0.3M $CaCl_2$ solution and mixed. This solution was added to an equal volume of Transfection Buffer (0.28M NaCl, 0.05M HEPES, 1.5 mM $Na_2HPO_4$, pH 7.10). The total volume of the combined solutions was 300 milliliters.

Following mixing, 30 milliliters of the Transfection solution containing plasmids was added to each of the ten roller bottles (corresponding to addition of 150 µg of each of the three plasmids to each roller bottle). The bottles returned to the roller bottle rack for a further incubation period of approximately 16 hours (overnight). After incubation, the roller bottles were removed from the roller bottle rack, and placed in a BSC.

For each roller bottle, the growth medium was completely removed, taking care not to disrupt adherent cells growing on the walls of the vessels. The growth medium was removed and replaced with pre-warmed (37° C.) DMEM supplemented with 1 mM glutamine, but not supplemented with FCS. The roller bottles were returned to the roller bottle rack, and incubated for a further three days at 37° C. After incubation, the roller bottles were removed from the roller bottle rack and placed in a BSC. Two milliliters of 0.5M ethylene diamine tetraacetate (EDTA) were added to each bottle (final concentration of EDTA in growth medium was 5 mM), and bottles were gently agitated to remove cells from the inside surface of the roller bottle. After complete detachment, the cells containing AAV were removed from the roller bottles and AAV production was assessed using Q-PCR. Although AAV production using this method is generally in the range of $5 \times 10^9$–$1 \times 10^{10}$ vg/cm$^2$ for a roller bottle having a surface area of 850 cm$^2$, in this particular example AAV production was $6.5 \times 10^9$ vg/cm$^2$. As shown in FIG. 3, AAV produced using similar techniques, but in T-flasks having a surface area of 225 cm$^2$, yields only about $2.3 \times 10^9$ vg/cm$^2$. Following assessment of AAV production, the cells were pooled in a sterile container for further processing.

The manipulation of roller bottles as described in this example can be performed manually by trained personnel using appropriate equipment to ensure the sterility of the cultures. For manipulations of larger numbers of bottles (for example, greater than or equal to 100 roller bottles), the use of equipment designed for automation of roller bottle handling can be used. One such apparatus is The Automation Partnership CellMate™ robot arm. For example, for performing each of the manipulations described above for 500 roller bottles, use of the CellMate™ robot arm (assembled and distributed by The Automation Partnership, Boston Mass.) would replace skilled operators. Advantages of using this automation system include capability to handle more roller bottles, higher precision of manipulations, reduced incidence of contamination, and reduced incidence of personnel injury.

Example 2

Concentration of rAAV-Containing Cells

Although not essential to the purification of rAAV, cells harvested in the cell culture media (DMEM medium) were concentrated using continuous centrifugation. Cells and cell culture medium were fed in the centrifuge through the input valve continuously, and concentrated down by low speed centrifugation (1000 rpm to 1200 rpm). The concentrated cells were continuously harvested from the centrifuge from the bottom of the container to a cell collection container. The waste medium was discharged from the top of the centrifuge to the waste container. Since this centrifuge allows the materials to be continuously fed in and the waste materials continuously discharged, high throughput was achieved. Using continuous centrifugation, a 15-fold volume reduction was achieved.

Example 3

Buffer Exchange

Although also not essential to the purification of rAAV, the procedure described in Example 2 was used to exchange the culture medium in which the cells were grown with a buffer solution of choice. The starting buffer being used for rAAV purification column chromatography techniques contains 20 mM sodium phosphate and 200 mM sodium chloride at pH 5.5 or higher. The high throughput of the continuous centrifugation allows greater than 90% buffer exchange of rAAV-containing cell solutions.

Example 4

Lysis of Concentrated Culture Medium

Figure 4:
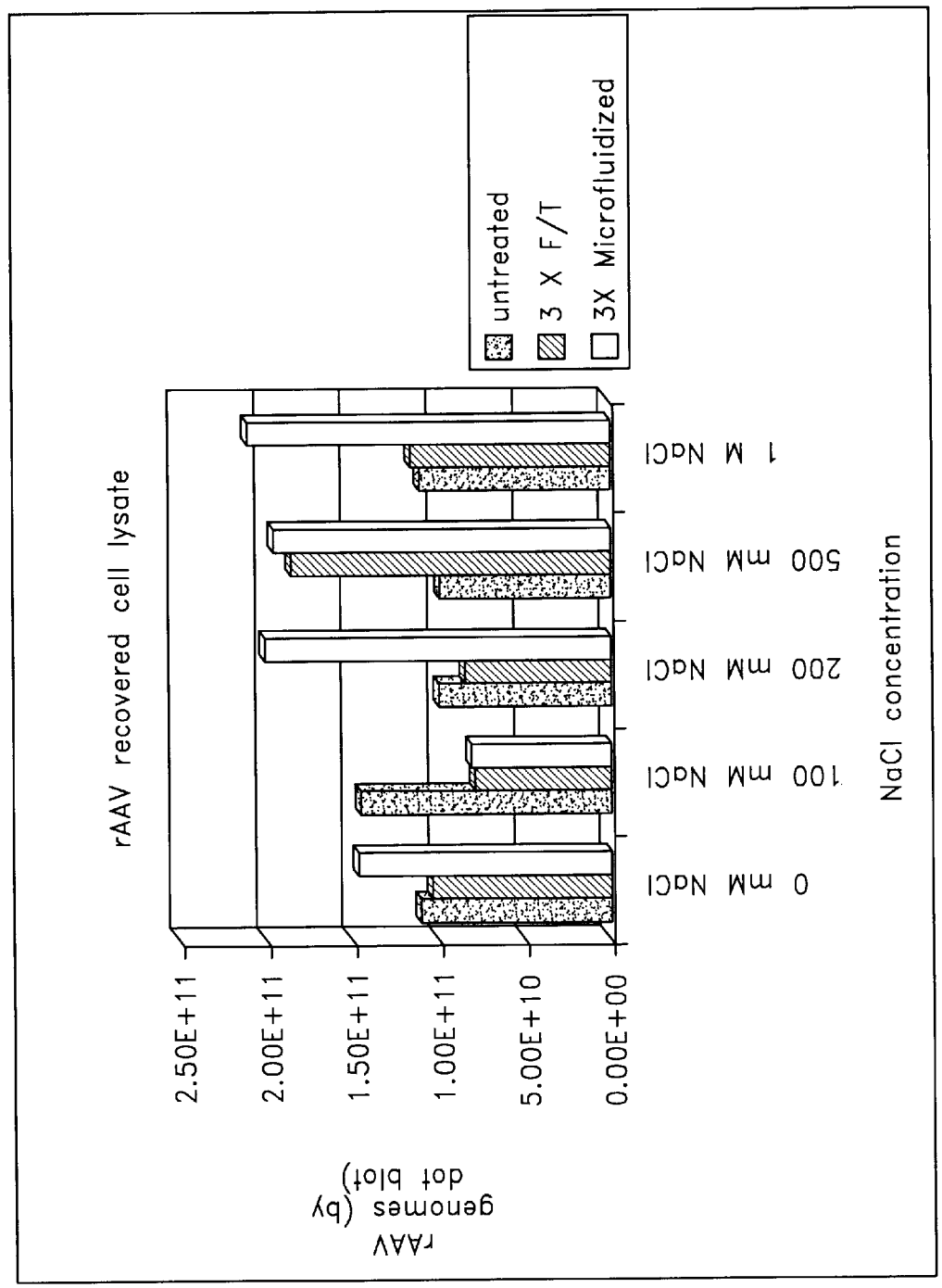
FIG. 4 is a comparison rAAV genome recovery following cell lysis by freeze/thaw versus microfluidization.

For large-scale rAAV purification, the cells were lysed using a microfluidization technique. Recovery using this technique was also compared to that obtained using freeze/thaw lysis techniques. As shown in FIG. 4, rAAV is more efficiently recovered after three rounds of microfluidization than after three freeze/thaw rounds over a variety of salt concentrations. Also, regardless which technique is used, the salt concentration affected the efficiency of viral vector release from cells. Specifically, when sodium chloride in the range of 200–1000 mM was used, the rAAV vectors were extracted more efficiently than under lower salt conditions.

Figure 5:
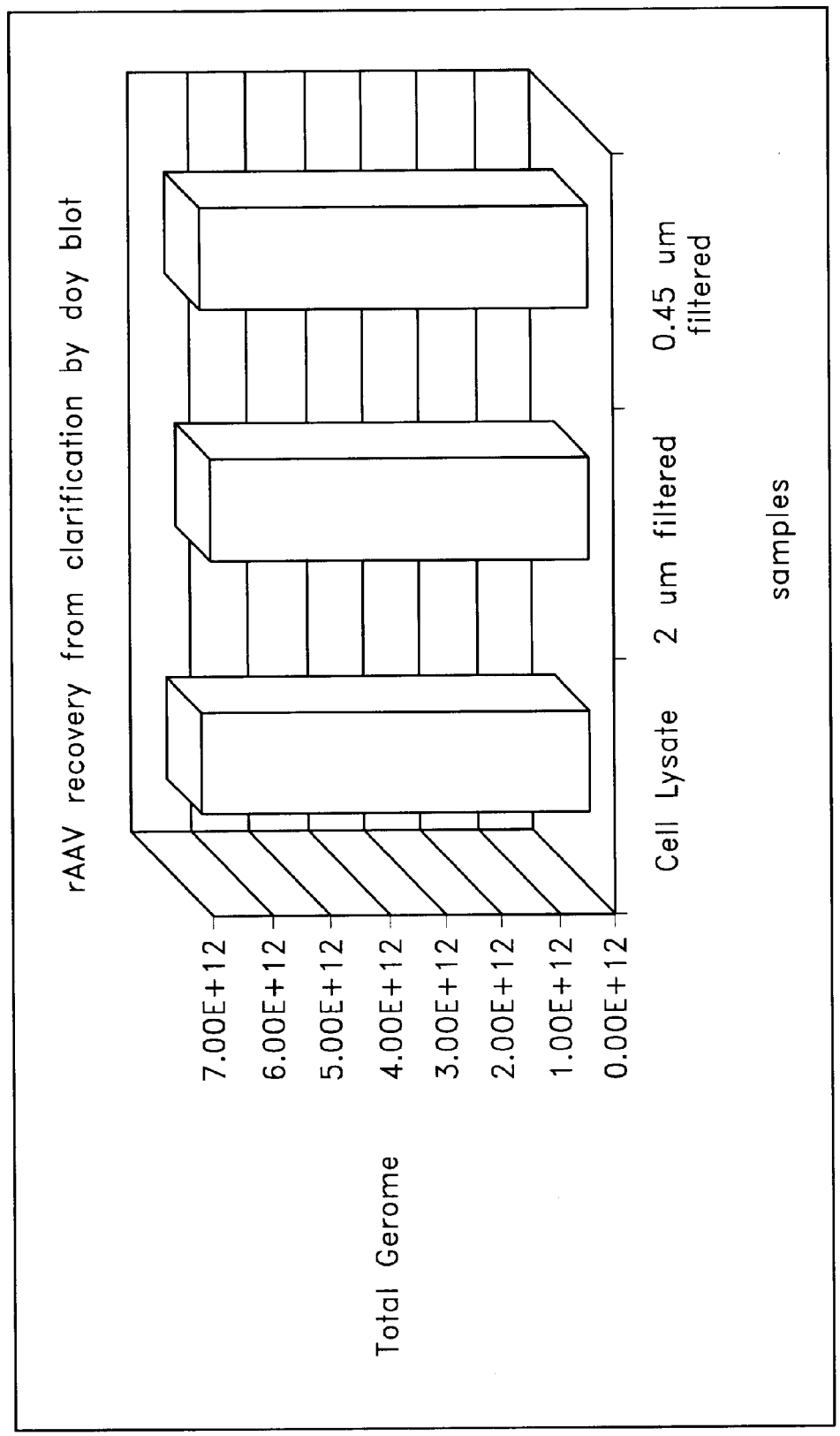
FIG. 5 shows the results of a dot blot comparison of rAAV recovery after clarification using various filters.
Figure 6:
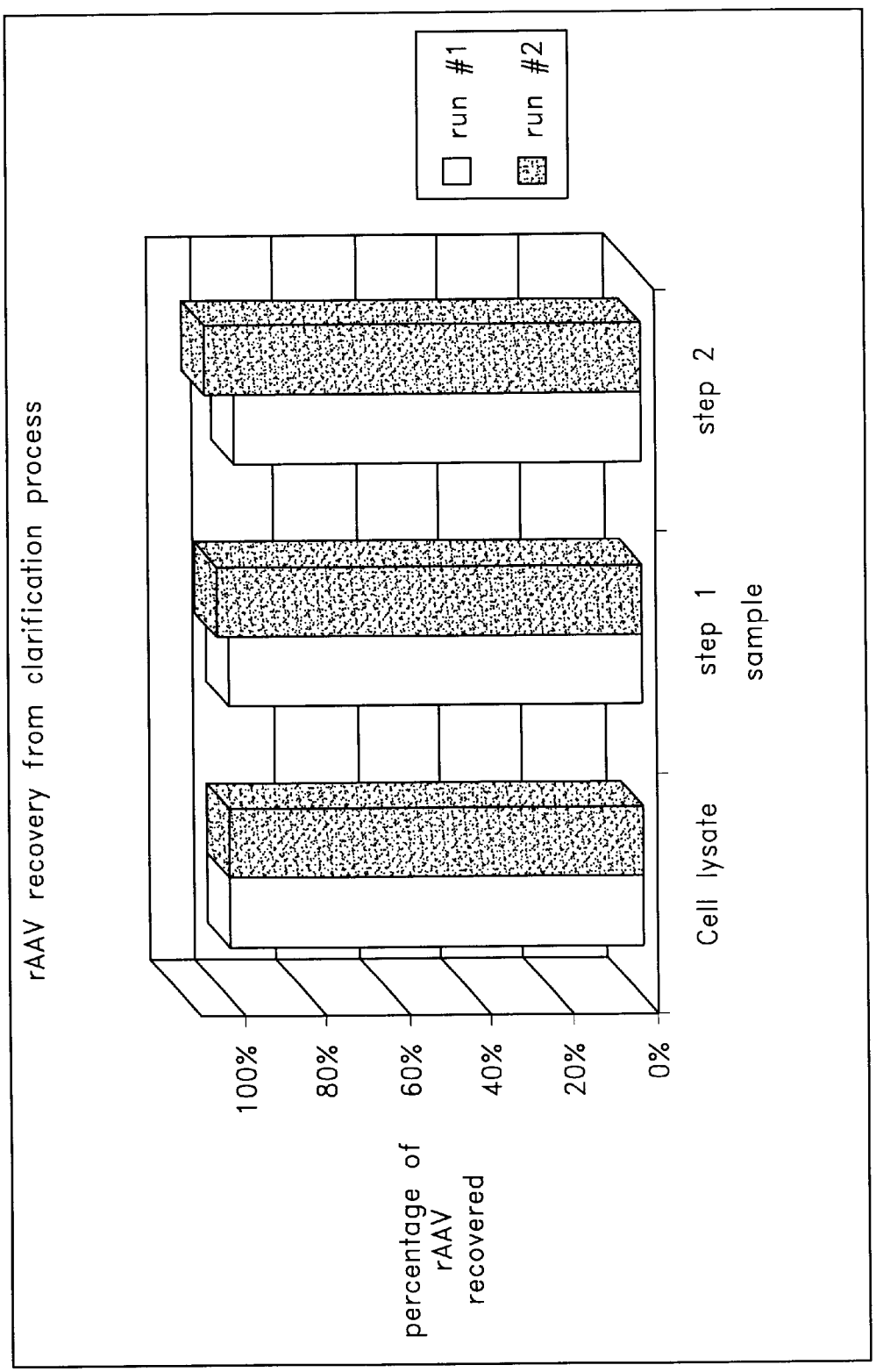
FIG. 6 shows the percentage of rAAV following clarification.
Figure 7:
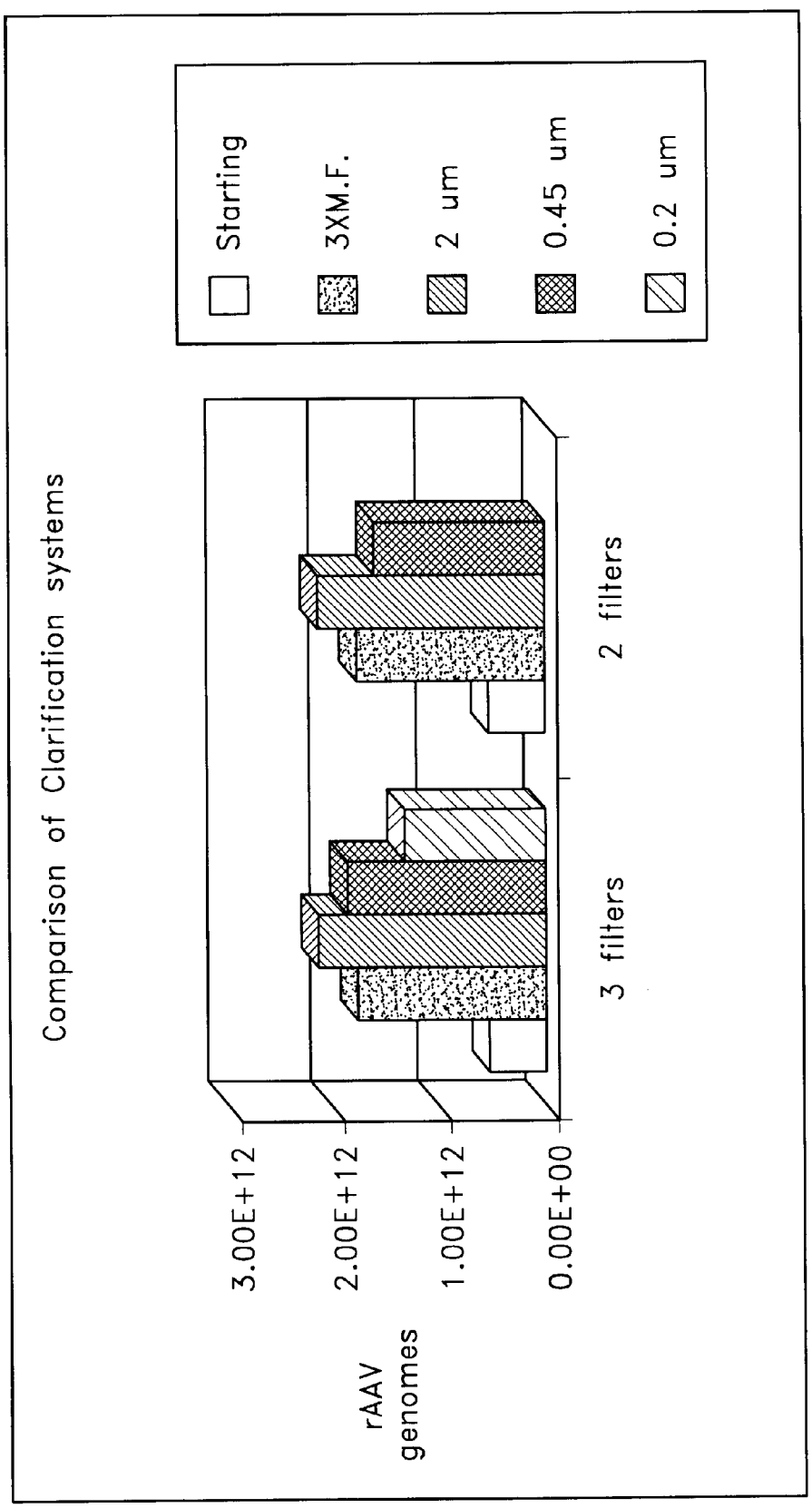
FIG. 7 is a comparison of rAAV recovery following filtration using two filters versus three filters.

Although not an essential step, following lysis, the cell lysate was then treated with BENZONASE™ to digest the genomic DNA (described in detail in Example 5 below). After the nuclease treatment, the lysate was further clarified by filtration. That is, the cell lysate was sequentially filtered at a flow rate of about 350 ml/min through two filters having pore sizes of 2 $\mu$m (ULTIPLEAT PROFILE™; surface area of approximately 2400 cm$^2$) and 0.45 $\mu$m (SUPORLIFE™; 450 DCF, surface area of approximately 1000 cm$^2$) (Pall Membrane Technology Corporation, Pensacola, Fla.). As shown in FIG. 5, recovery of rAAV was greater than 90% throughout this clarification process. This high level of rAAV recovery was confirmed in two subsequent filtration runs. Specifically, as shown in FIG. 6, filtration through a filter having 2 $\mu$m pore size (Step 1) yielded greater than 90% recovery for both runs #1 and #2, and filtration through a filter having 0.45 $\mu$m pore size (Step 2) also yielded greater than 90% recovery for both runs #1 and #2. Furthermore, as shown in FIG. 7, a comparison of a clarification system using only a 2 $\mu$m and 0.2 $\mu$m (SUPORLIFE™; 200 DCF, surface area of approximately 1000 cm$^2$) filter to a clarification system using a 2 $\mu$m, 0.45 $\mu$m, and 0.2 $\mu$m filter showed that rAAV recovery is somewhat better using a two-filter system rather than a three filter system.

Example 5

Nuclease Digestion of Lysate

BENZONASE™, an endonuclease, was used to digest the genomic DNA at room temperature (approximately 37° C.). The efficiency of DNA digestion was compared in two buffer systems, Buffer A composed of 20 mM sodium phosphate/200 mM sodium chloride/2 mM MgCl$_2$ at pH 5.5, and Buffer B composed of 50 mM Tris/2 mM MgCl$_2$ at pH 8.5. Use of either Buffer A or Buffer B with 200 U/ml BENZONASE resulted in the majority of the genomic DNA being digested to smaller than 800 base pairs.

Example 6

Cation Exchange Chromatography of Concentrated Culture Medium

Figure 8:
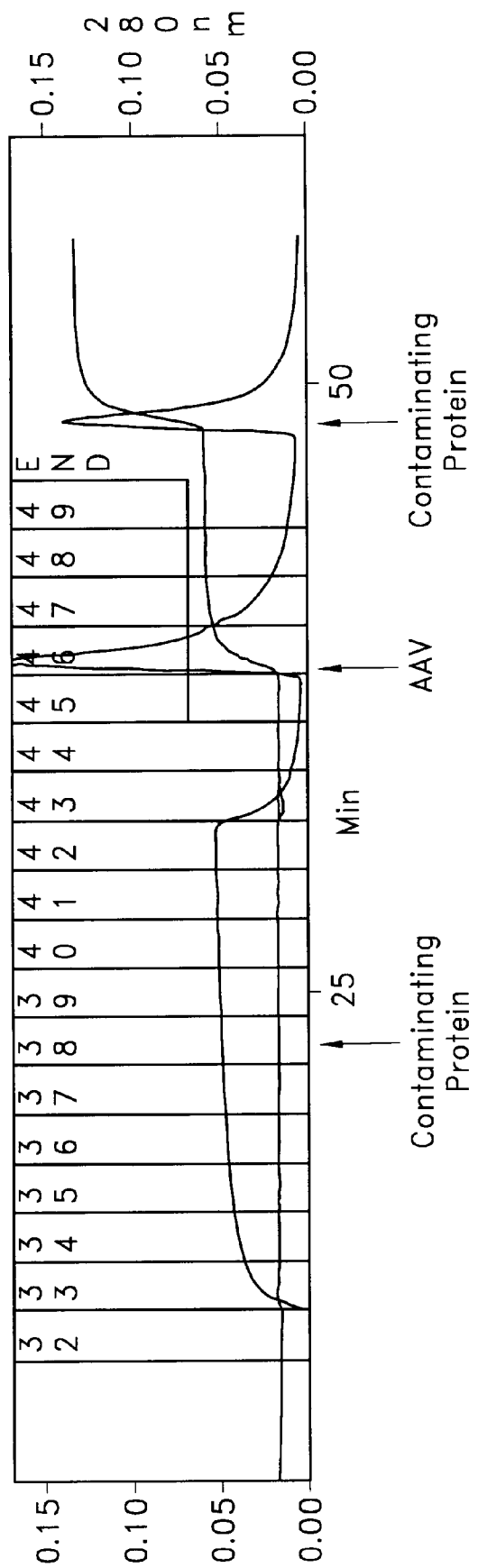
FIG. 8 is a cation exchange chromatography elution profile of rAAV-containing material.

The cell lysate from five roller bottles (approximately one liter without concentration) was loaded on a 10 ml cation exchanger module containing the MUSTANG S™ medium (Pall Corporation, Port Washington, N.Y.). FIG. 8 is the elution profile of total protein as detected spectrophotometrically by measuring absorbance at a 280 nm wavelength. The cell lysate was added to the column after the column was equilibrated with loading buffer for 3 bed volumes. A sample prepared in accordance with the previous Examples 1 and 4 was adjusted to 20 mM sodium phosphate, 100 mM sodium chloride 5.5 and loaded on the column at a flow rate of 5 ml/min. The column was then washed with 3 bed volumes of the loading buffer at the same flow rate resulting in a significant amount of the unbound protein being washed from the column. The broad peak between about 12 and 32 minutes represents this contaminating protein. Following the wash, the rAAV was eluted from the column with 3 bed volumes of 20 mM sodium phosphate/300 mM sodium chloride at a pH of 5.5. The peak at about 38 minutes in FIG. 8 represents AAV as later determined by infectious activity and genome titer. The column was then cleaned with 1M sodium chloride/20 mM sodium phosphate buffer to remove remaining protein (represented by the peak at about 48 minutes in FIG. 8). Approximately 80–90% of the rAAV loaded onto the column was recovered as determined by dot blot.

Example 7

Affinity Chromatography of Concentrated Culture Medium

Figure 9:
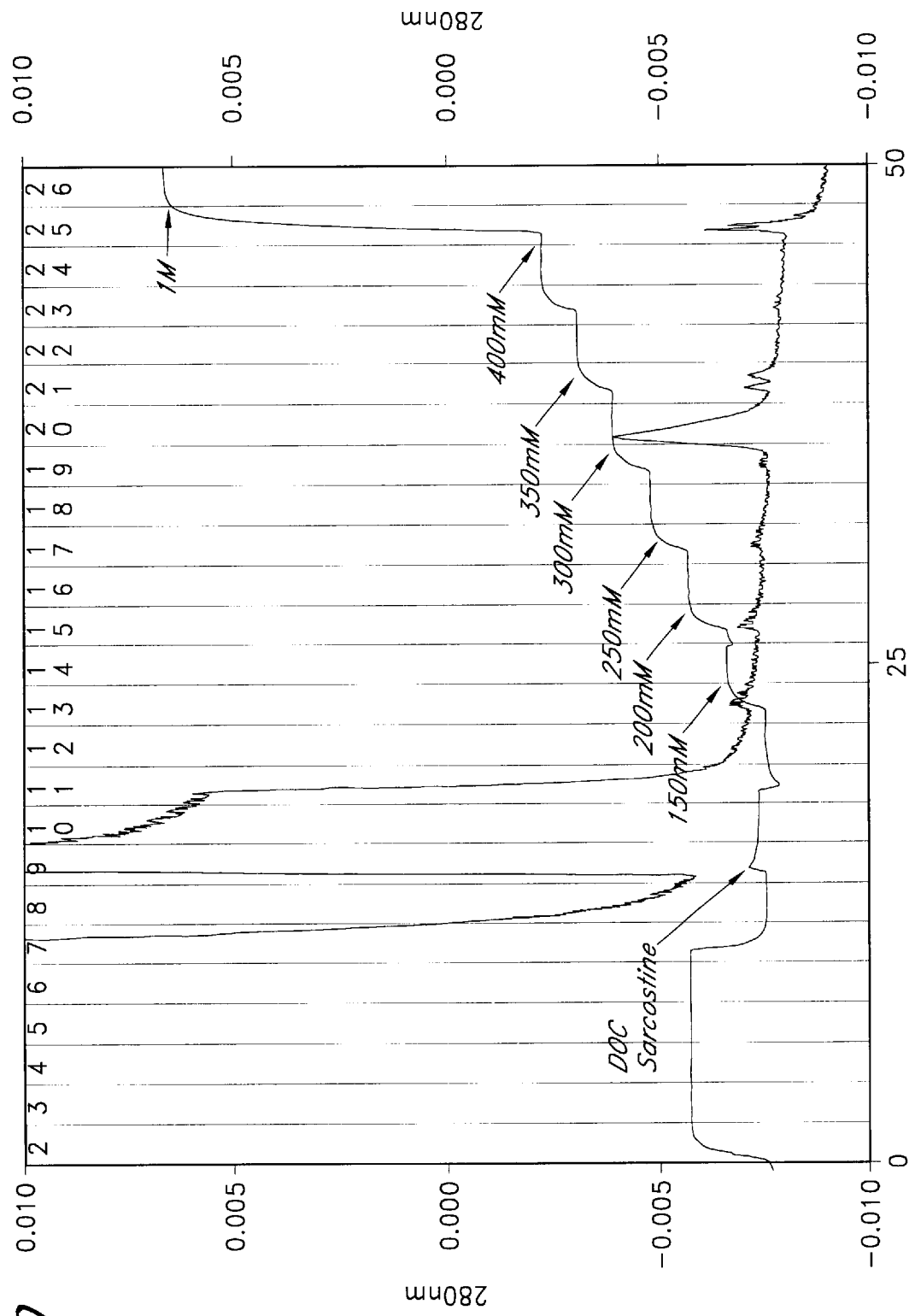
FIG. 9 is a heparin-based affinity chromatography elution profile of rAAV-containing material.

In this Example, a heparin-based resin called POROS 20HE™ was used in an affinity column for rAAV purification. This column is commercially available in 1.6 mL or 30 mL sizes and has a capacity of approximately $1.5$–$3.0 \times 10^{12}$ vector genomes per mL. The rAAV eluted from the cation exchanger in Example 6 was applied to the heparin column in the same buffer at a flow rate of 150 cm/hr but at a salt concentration of 200 mM sodium chloride. The column was then washed several times with the following buffers for 3-bed volumes each: 20 mM sodium phosphate/100 mM sodium chloride buffer at pH 5.5; 20 mM sodium phosphate/200 mM sodium chloride/5 mM sarcosine at pH 5.5; 20 mM sodium phosphate/100 mM sodium chloride buffer at pH 5.5; 20 mM sodium phosphate/150 mM sodium chloride buffer at pH 5.5; 20 mM sodium phosphate/200 mM sodium chloride buffer at pH 5.5; 20 mM sodium phosphate/250 mM sodium chloride buffer at pH 5.5; 20 mM sodium phosphate/300 mM sodium chloride buffer at pH 5.5; 20 mM sodium phosphate/350 mM sodium chloride buffer at pH 5.5; and 20 mM sodium phosphate/400 mM sodium chloride buffer at pH 5.5. As indicated in the elution profile shown in FIG. 9, AAV was eluted using 300 mM and 350 mM sodium chloride. Peaks corresponding to washes at other salt concentrations represent protein contamination. The column was cleaned with a buffer containing 20 mM sodium phosphate/1 M sodium chloride buffer at pH 5.5. A purified sample of virions (1E+10 rAAV particles) was analyzed by silver-stained SDS-PAGE for purity and only rAAV capsid proteins were detected.

Example 8

Anion Exchange Chromatography of Lysate

Figure 10:
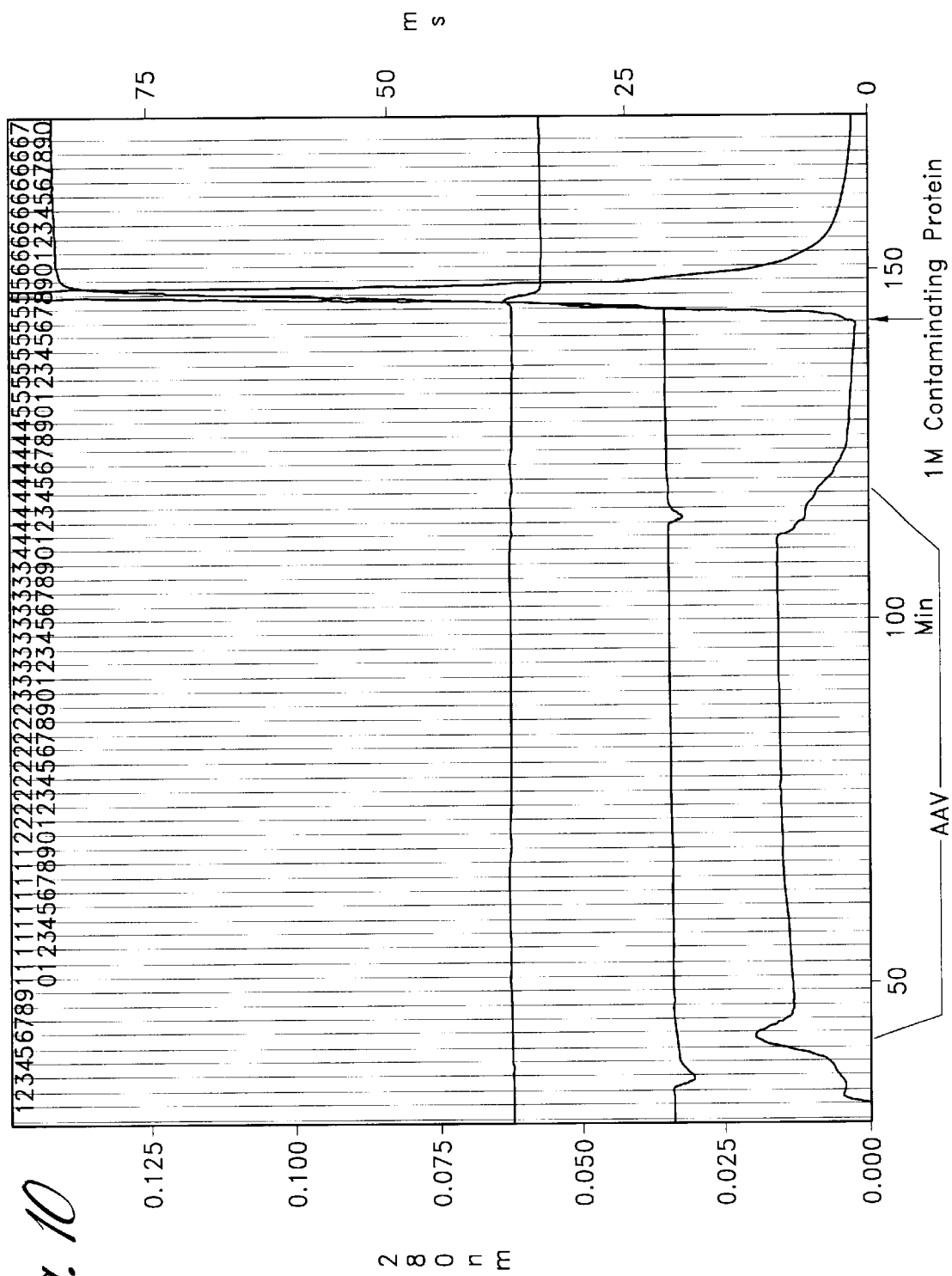
FIG. 10 is an anion exchange chromatography elution profile of rAAV-containing material showing rAAV recovery in the flow through fractions as well as removal of contaminating protein.

In this Example, an anion exchange column containing the resin STREAMLINE Q XL™ (Pharmacia) was used to purify rAAV. 200 mL cell lysate prepared according to the methods described in Examples 1 and 4 was purified over a 30 mL column. Specifically, the salt concentration and pH of the lysate was adjusted to 200 mM NaCl and 7.4, respectively. The sample was then loaded on the column at a flow rate of 300 cm/hr. Also, three bed volumes of 20 mM sodium phosphate/200 mM sodium chloride at pH 7.4 was added resulting in a significant amount of the unbound protein being washed off the column. The elution profile (FIG. 10) shows the total protein as detected spectrophotometrically by measuring absorbance at a 280 nm wavelength. It was determined by virus infectious activity and virus genome titration that rAAV is present in the flow through fractions, corresponding to the broad peak between about 40–120 minutes. This purification step resulted in about a 2–3-fold reduction of contaminating protein and about 100-fold reduction in contaminating nucleic acid. The column was cleaned with a buffer containing 20 mM sodium phosphate/1 M sodium chloride, resulting in the release of a significant amount of contaminating protein from the column (corresponding to the peak at about 144 minutes).

Figure 11A:
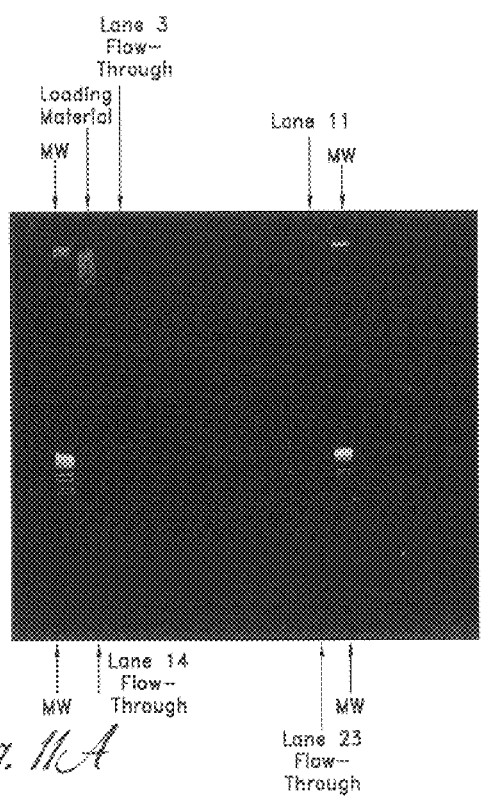
FIG. 11 shows the removal of nucleic acids through anion exchange chromatography by agarose gel electrophoresis.
Figure 11B:
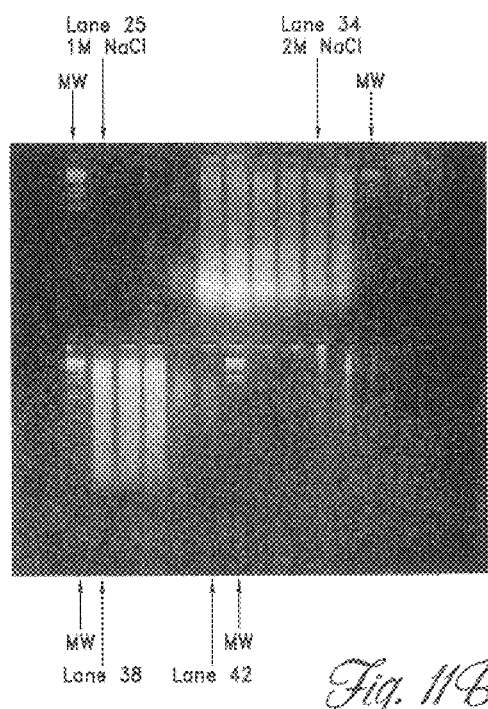

As demonstrated by agarose gel electrophoresis (FIG. 11), the anion exchange column efficiently removed a significant amount of nucleic acid from the cell lysate. Specifically, no nucleic acid was detected in the flow through fractions (lanes 3–11 and 14–23) using this technique. A significant amount of contaminating nucleic acid did come off the column in the 1M sodium chloride wash, corresponding to lanes 26–33, and in a further 2 M sodium chloride wash corresponding to lanes 34–35 and 38–42.

Figure 12:
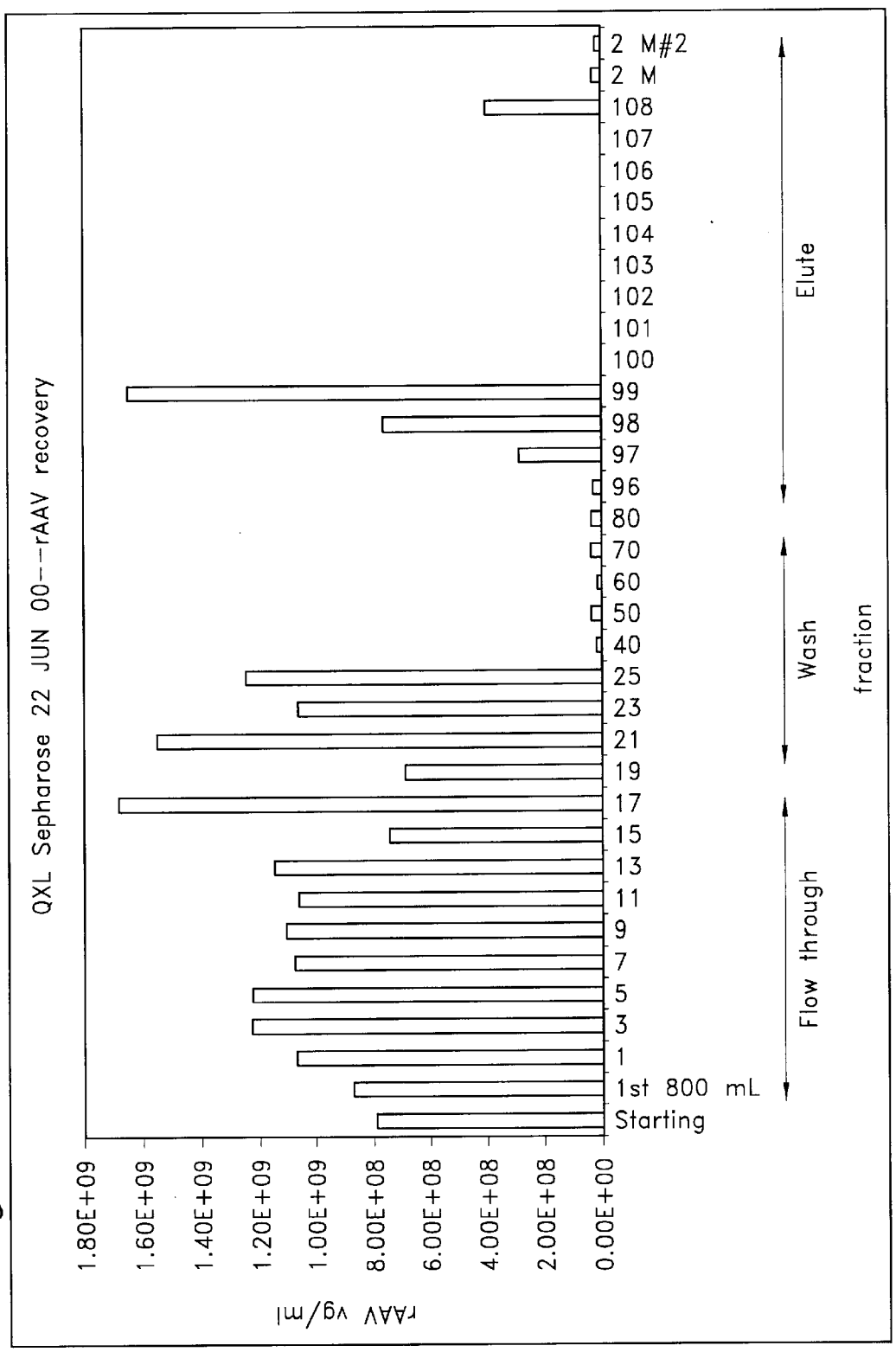
FIG. 12 is the Q-PCR analysis of anion exchange chromatography fractions.

Blue cell assays of the purified fractions confirmed that rAAV-lacZ passed through the resin. Also, as shown in FIG. 12, Q-PCR analysis revealed that greater than 90% of the rAAV could be recovered in the flow-through fractions. Other contaminating cellular materials were likely also removed from the rAAV preparation, including RNA and lipids. Following passage over the anion exchange resin, the flow-through fractions were collected for further purification or storage.

Example 9

Ultrafiltration/Diafiltration (UF/DF) of Column Purified Material

The material obtained following column chromatography purification using a heparin-based resin was concentrated two-fold and ultrafiltered using ten diafiltration volumes to exchange the column elution buffer with phosphate-buffed saline, pH 7.1, containing 5% sorbitol, a buffer formulation compatible with in vivo injection. The apparatus used for UD/DF was a hollowfibre-based system termed the MidGee, manufactured by A/G Technology Corporation. The recovery of AAV vector following UF/DF step was in the range from 60%–90%.

Example 10

Anion Exchange and Heparin Column Purification

In this Example, rAAV was prepared according to the previous Examples with the exceptions that no cation exchange column was used and the lysate was not treated with BENZONASE™. Rather, the cells were grown and transfected as in Example 1, lysed as in Example 4, the rAAV-containing material was passed over an anion exchange column as in Example 8, run on a heparin sulfate affinity column as in Example 7, and eluted as in Example 7. The yields obtained in each step were comparable to those obtained in each individual Example, and the final rAAV purity was assessed by SDS PAGE gel electrophoresis.

Figure 13:
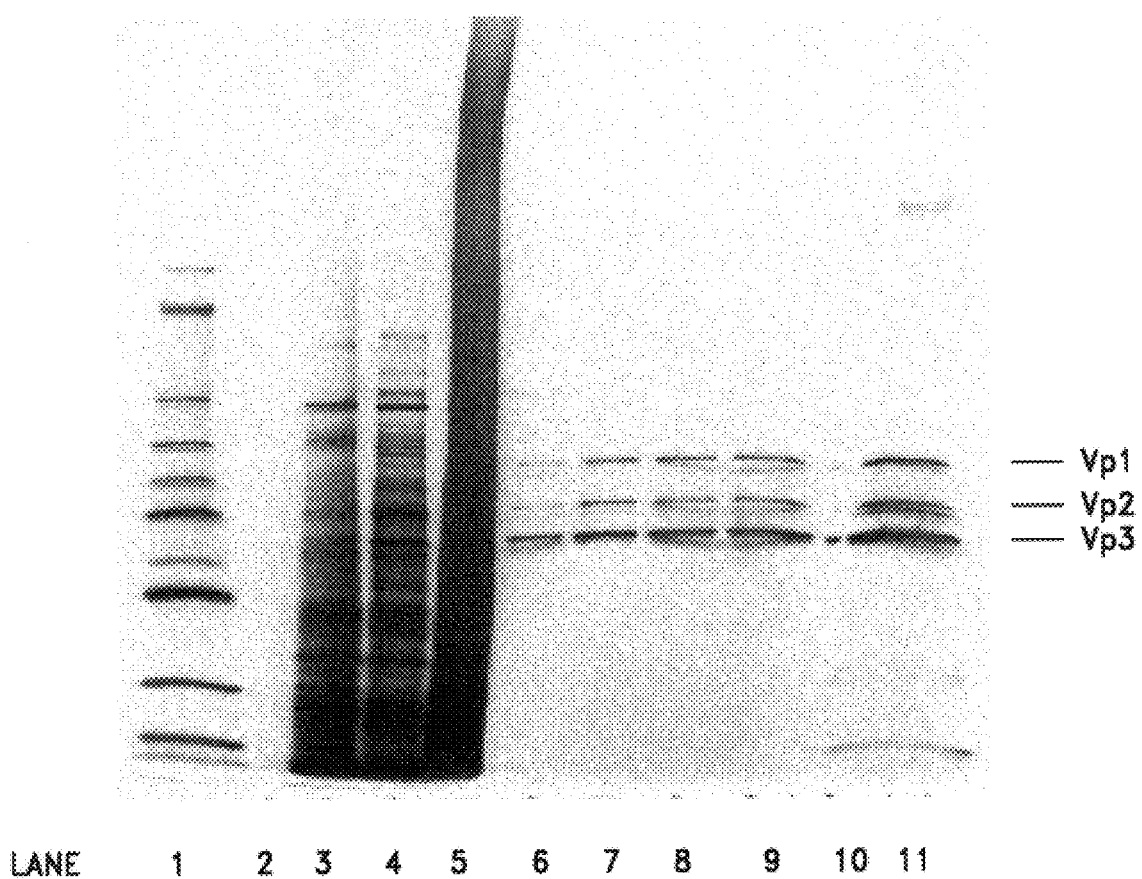
FIG. 13 is a comparison of column-purified rAAV with CsCl purified rAAV by silver-stained SDS-PAGE.

Referring to FIG. 13, various fractions from the column purifications were analyzed by SDS-PAGE. Lane one shows a molecular weight marker, lane two is empty, lane 3 shows 5 ul of the flow through from the anion exchange column, lane 4 shows 4 ul of the flow through material from the heparin sulfate column, lane 5 shows the material from a 0.50% DOC wash of the heparin sulfate column, lanes 6–9 shows 5, 10, 15, and 20 mL, respectively, of rAAV-containing material from the purified fractions after 100-fold concentration in a Centricon™ column (Millipore, Bedford, Mass.), lane 10 is empty, and lane eleven is a CsCl purified control. The column-purified fractions (lanes 6–9) yielded bands corresponding to VP1, VP2, and VP3 having comparable purity to the CsCl-purified control.

Figure 14:
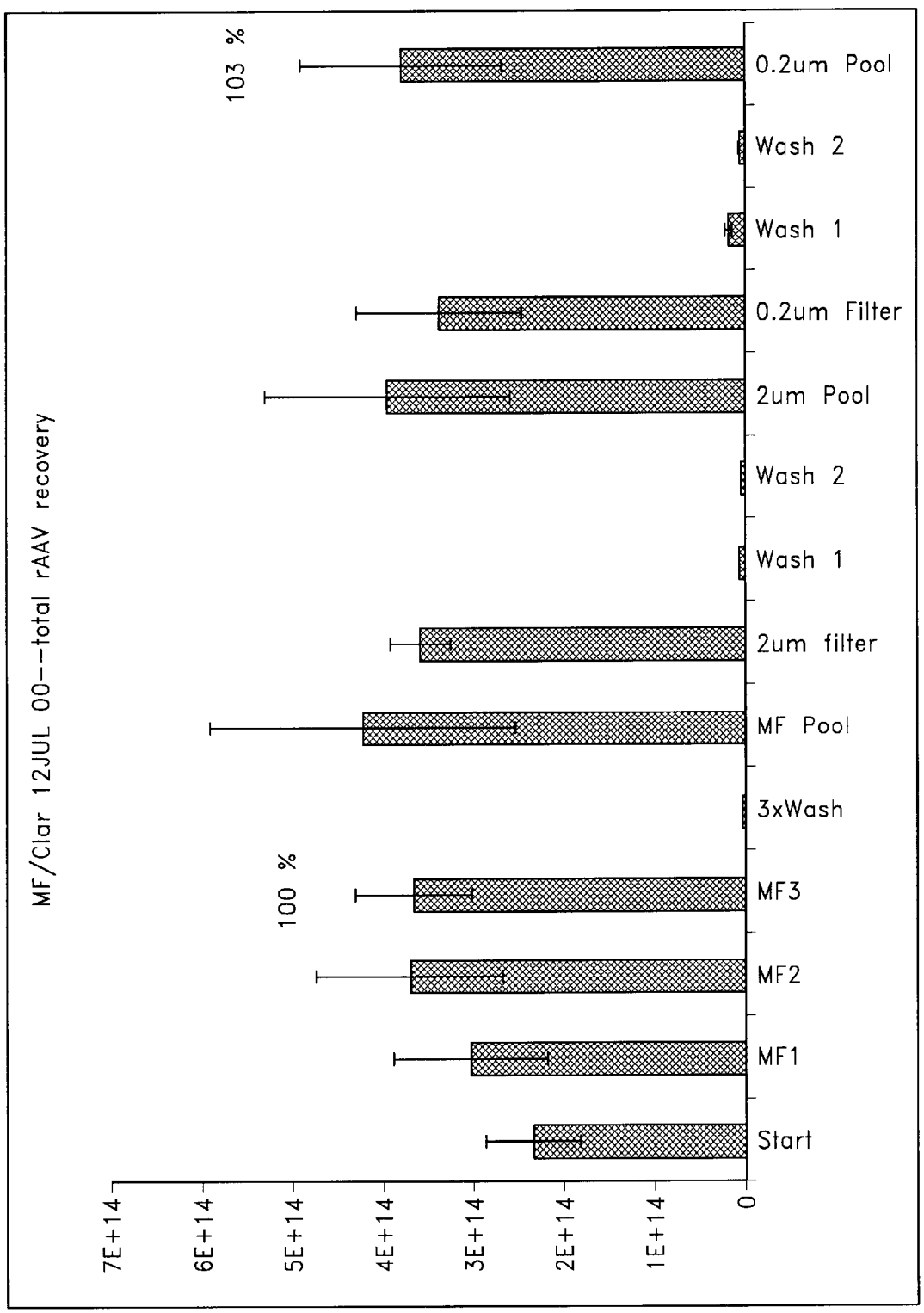
FIG. 14 shows recovery of AAV at each step throughout a purification process using an anion exchange column and a heparin column.

The recovery of AAV at each step throughout this purification process is shown in FIG. 14. Specifically, virion recovery is shown for each of three rounds of microfluidization, for filtration through a 2 um filter, for two washes of this filter, for the pooled filtrate and wash materials, for filtration through a 0.2 um filter as well as for two washes of this filter, and for the pooled filtrate and wash materials (these steps were performed according to Example 4). Virion recovery is also shown for the anion exchange column flow-through fraction, for the wash material, and for the 1 M NaCl and 2 M NaCl eluate (performed according to Example 8). Finally, virion recovery is shown for the heparin column flow-through fraction, various washes, and eluate fractions (performed according to Example 7). rAAV recovery was monitored using real-time quantitative PCR of representative samples for each of these major steps in the purification process. It was found that more than 80% of the total rAAV virions contained in the starting materials were recovered in the final product.

CONCLUSION

All publications, patents and patent applications cited herein are hereby incorporated by reference in their entirety. As used in this specification and the appended claims, the singular forms "a," "an," and "the" include plural references unless the content clearly dictates otherwise. Although the invention has been described with reference to various embodiments, it should be understood that various modifications can be made without departing from the spirit of the invention. Accordingly, the invention is limited only by the following claims.

What is claimed is:

1. A method of purifying recombinant AAV (rAAV) virions from contaminants, comprising:
   (a) introducing an AAV vector into a suitable host cell;
   (b) introducing a first nucleic acid comprising AAV helper function coding regions that are expressed in the host cell to complement AAV helper functions missing from said AAV vector, and a second nucleic acid that comprises regions encoding accessory functions, wherein said second nucleic acid and said host cell collectively lack a gene necessary for adenovirus production;
   (c) culturing the host cell to produce rAAV virions;
   (d) preparing a lysate from said host cell provided in step (a);
   (e) passing the lysate over an anion exchange chromatography medium, thereby binding said contaminants to said anion exchange chromatography medium;
   (f) collecting a flow-through containing rAAV;
   (g) passing the flow-through over an affinity chromatography medium;
   (h) washing the affinity chromatography medium with an anionic detergent comprising sarcosine, and
   (i) eluting purified rAAV from said affinity chromatography medium after step (h).

2. The method of claim 1, wherein said lysate is passed over said anion exchange chromatography medium first and said affinity chromatography medium second.

3. The method of claim 1, wherein said lysate is passed over said affinity chromatography medium first and said anion exchange chromatography medium second.

4. The method of claim 1, wherein said affinity chromatography medium comprises an AAV binding molecule selected from the group consisting of an AAV receptor and an antibody with binding affinity for AAV.

5. The method of claim 4, wherein said affinity chromatography medium is heparin sulfate.

6. The method of claim 1, wherein said lysate is prepared by microfluidization of said host cell line.

7. The method of claim 1, further comprising filtering the lysate.

8. The method of claim 1, wherein said host cell line was cultured substantially serum-free.

9. The method of claim 1, further comprising treating the lysate with a nuclease.

10. The method of claim 1, wherein said host cell line was cultured in a bioreactor.

11. The method of claim 1, wherein said host cell line was transfected with an accessory function vector, an AAV vector, and an AAV helper vector.

12. A method of purifying recombinant AAV (rAAV) virions, from contaminants comprising:
   (a) providing a host cell comprising rAAV virions;
   (b) preparing a lysate from said cell provided in step (a);
   (c) passing the lysate over a cation exchange chromatography medium, thereby binding said rAAV to said cation exchange chromatography medium;
   (d) washing said bound rAAV of said cation exchange chromatography medium;
   (e) collecting an eluate obtained in step (d);
   (f) passing said eluate over an affinity chromatography medium;
   (g) washing the affinity chromatography medium with an anionic detergent comprising sarcosine; and
   (i) eluting purified rAAV from said affinity chromatography medium after step (g).

13. The method of claim 12, wherein said lysate is passed over said affinity chromatography medium first and said cation exchange chromatography medium second.

14. The method of claim 12, wherein said cation exchange chromatography medium is selected from the group consisting of sulfo-, phospho, carboxy-, and carboxy-methyl-based resins.

15. The method of claim 12, wherein said affinity chromatography medium comprises heparin sulfate.

16. The method of claim 12, wherein said lysate is passed over said cation exchange chromatography medium first and said affinity chromatography medium second.

17. The method of claim 12, wherein said lysate is passed over said affinity chromatography medium first and said cation exchange chromatography medium second.

18. The method of claim 12, wherein said affinity chromatography medium comprises an AAV binding molecule selected from the group consisting of an AAV receptor and an antibody with binding affinity for AAV.

19. The method of claim 18, wherein said affinity chromatography medium is heparin sulfate.

20. A method of purifying recombinant AAV (rAAV) virions from contaminants, comprising:
   (a) providing a host cell comprising rAAV virions;
   (b) preparing a lysate from said cell provided in step (a);
   (c) passing the lysate over a cation exchange chromatography medium, thereby binding said rAAV to said cation exchange chromatography medium;
   (d) washing said bound rAAV of said cation exchange chromatography medium;
   (e) collecting an eluate obtained in step (d);
   (f) passing said eluate over an anion exchange chromatography medium, thereby binding said contaminants to said anion exchange chromatography medium;
   (g) passing the eluate obtained in step (f) over an affinity chromatography medium; and
   (h) washing the affinity exchange chromatography medium with an anionic detergent comprising sarcosine; and
   (i) eluting purified rAAV from said affinity chromatography medium after step (h).

21. The method of claim 1, wherein the first and second nucleic acids are on separate vectors.

* * * * *

UNITED STATES PATENT AND TRADEMARK OFFICE
CERTIFICATE OF CORRECTION

PATENT NO. : 6,593,123 B1
DATED : July 15, 2003
INVENTOR(S) : John Fraser Wright and Guang Qu It is certified that error appears in the above-identified patent and that said Letters Patent is hereby corrected as shown below:

Title page,
Item [75], Inventor name "Quang Qu" should read -- Guang Qu --

Column 1,
Line 43, the word "sing-stranded" should read -- single stranded --

Column 6,
Line 52, the word "ease" should read -- disease --

Column 9,
Line 66, "device,the" should read -- device, the --

Column 10,
Line 49, delete the comma after the word "sequence"

Column 12,
Line 58, the word "phosphor" should be -- phospho --

Signed and Sealed this

Fourteenth Day of October, 2003

JAMES E. ROGAN
*Director of the United States Patent and Trademark Office*